(12) United States Patent
Malkoch et al.

(10) Patent No.: US 11,684,554 B2
(45) Date of Patent: *Jun. 27, 2023

(54) COMPOSITION COMPRISING THIOL, ALKENE AND PHOSPHONIC ACID CONTAINING COMPOUNDS FOR USE AS A PRIMER FOR ADHESION IMPROVEMENT

(71) Applicant: BIOMEDICAL BONDING AB, Täby (SE)

(72) Inventors: Michael Malkoch, Täby (SE); Viktor Granskog, Danderyd (SE); Sandra Garcia Gallego, Guadalajara (ES); Mathieu Arseneault, Québec (CA)

(73) Assignee: BIOMEDICAL BONDING AB, Taby (SE)

( * ) Notice: Subject to any disclaimer, the term of this patent is extended or adjusted under 35 U.S.C. 154(b) by 346 days.

This patent is subject to a terminal disclaimer.

(21) Appl. No.: 16/759,157

(22) PCT Filed: Oct. 25, 2018

(86) PCT No.: PCT/EP2018/079289
§ 371 (c)(1),
(2) Date: Apr. 24, 2020

(87) PCT Pub. No.: WO2019/081641
PCT Pub. Date: May 2, 2019

(65) Prior Publication Data
US 2021/0170070 A1    Jun. 10, 2021

(30) Foreign Application Priority Data
Oct. 25, 2017    (WO) ................ PCT/EP2017/077350

(51) Int. Cl.
*A61K 6/40*    (2020.01)
*A61K 6/62*    (2020.01)
(Continued)

(52) U.S. Cl.
CPC ............ *A61K 6/40* (2020.01); *A61B 17/8836* (2013.01); *A61C 19/004* (2013.01); *A61K 6/62* (2020.01);
(Continued)

(58) Field of Classification Search
None
See application file for complete search history.

(56) References Cited

U.S. PATENT DOCUMENTS

| 2011/0195876 A1 | 8/2011 | Heath et al. |
| 2013/0123381 A1* | 5/2013 | Bowman ................ C08G 75/12 522/42 |

(Continued)

FOREIGN PATENT DOCUMENTS

| WO | 2011/048077 A2 | 4/2011 |
| WO | 2012/126695 A1 | 9/2012 |

(Continued)

OTHER PUBLICATIONS

International Search Report for PCT/EP2018/079289, dated Jan. 15, 2019, 3 pages.

(Continued)

*Primary Examiner* — Michael F Pepitone
(74) *Attorney, Agent, or Firm* — Adsero IP

(57) ABSTRACT

The present invention relates to a primer composition that may be applied to tissue in order to increase bond strength between the tissue and a patch, filler or a supporting material. The primer comprises a dithiol component and an allyl containing component together with a photo initiator.

23 Claims, 13 Drawing Sheets

(51) Int. Cl.
*A61B 17/88* (2006.01)
*A61C 13/15* (2006.01)
*A61L 27/18* (2006.01)
*C08G 75/045* (2016.01)
*C08L 81/02* (2006.01)
*C09D 181/02* (2006.01)
*A61L 27/50* (2006.01)

(52) U.S. Cl.
CPC ............... *A61L 27/18* (2013.01); *A61L 27/50* (2013.01); *C08G 75/045* (2013.01); *C08L 81/02* (2013.01); *C09D 181/02* (2013.01); *A61B 2017/8838* (2013.01); *A61L 2430/02* (2013.01); *A61L 2430/12* (2013.01)

(56) References Cited

U.S. PATENT DOCUMENTS

| 2014/0296364 A1* | 10/2014 | Moszner | A61K 6/889 562/12 |
| 2016/0145392 A1* | 5/2016 | Toda | C08G 75/12 522/42 |
| 2020/0054533 A1 | 2/2020 | Malkoch et al. | |

FOREIGN PATENT DOCUMENTS

| WO | WO-2012126695 A1 * | 9/2012 | ........... G03F 7/0037 |
| WO | 2018/077973 A1 | 1/2018 | |
| WO | WO 2018/077973 A1 | 5/2018 | |

OTHER PUBLICATIONS

International Search Report for PCT/EP2017/077350, dated Jan. 31, 2018, 2 pages.
Office Action dated Aug. 18, 2022 with respect to U.S. Appl. No. 16/345,653.

* cited by examiner

| Primer Comp | Ace-tone wt% | Etha-nol wt% | Water wt% | LAP wt% | ETTMP wt% | BAPA wt% | Phn-G1-(ene)$_2$ wt% | (Phn)2-EDA-G1-(ene)$_2$ wt% | (Phn)2-HDA-G1-(ene)$_2$ wt% | Phn-G3-(ene)$_8$ wt% | H$_3$PO$_4$ wt% | TATATO wt% | TMPDE wt% | TMPSH wt% | TEMPIC wt% | Hexyne-TT wt% |
|---|---|---|---|---|---|---|---|---|---|---|---|---|---|---|---|---|
| P1a | - | 47.5 | 45.2 | 0.4 | 4.7 | 2.2 | - | 0.04 | - | - | - | - | - | - | - | - |
| P1b | - | 47.5 | 45.2 | 0.4 | 4.7 | 2.2 | - | 0.07 | - | - | - | - | - | - | - | - |
| P1c | - | 47.5 | 45.2 | 0.4 | 4.7 | 2.1 | - | 0.1 | - | - | - | - | - | - | - | - |
| P1d | - | 47.5 | 45.1 | 0.4 | 4.7 | 2.1 | - | 0.3 | - | - | - | - | - | - | - | - |
| P1e | - | 47.3 | 45 | 0.4 | 4.7 | 2 | - | 0.6 | - | - | - | - | - | - | - | - |
| P1f | - | 48.2 | 39.5 | 0.3 | 7.9 | 3.6 | - | 0.5 | - | - | - | - | - | - | - | - |
| P1g | - | 48.1 | 39.4 | 0.3 | 7.8 | 3.4 | - | 1 | - | - | - | - | - | - | - | - |
| P1h | - | 48 | 39.3 | 0.3 | 7.8 | 3.1 | - | 1.5 | - | - | - | - | - | - | - | - |
| P1i | - | 47.9 | 39.2 | 0.3 | 7.8 | 2.8 | - | 2 | - | - | - | - | - | - | - | - |
| P1j | - | 47.4 | 38.8 | 0.3 | 7.7 | 1.9 | - | 3.9 | - | - | - | - | - | - | - | - |
| P1k | - | 46.4 | 38 | 0.3 | 7.6 | - | - | 7.7 | - | - | - | - | - | - | - | - |
| P2a | - | 48.3 | 39.5 | 0.3 | 7.9 | 3.4 | 0.7 | - | - | - | - | - | - | - | - | - |
| P2b | - | 48.2 | 39.5 | 0.3 | 7.9 | 2.9 | 1.4 | - | - | - | - | - | - | - | - | - |
| P2c | - | 48 | 39.3 | 0.3 | 7.8 | 2.4 | 2.1 | - | - | - | - | - | - | - | - | - |
| P2d | - | 48 | 39.2 | 0.3 | 7.8 | 1.9 | 2.7 | - | - | - | - | - | - | - | - | - |
| P2e | - | 47.6 | 38.9 | 0.3 | 7.7 | - | 5.5 | - | - | - | - | - | - | - | - | - |
| P3a | - | 48.3 | 39.6 | 0.3 | 7.9 | 3.9 | - | - | - | - | - | - | - | - | - | - |

| Primer | Acetone | Ethanol | Water | LAP | ETTMP | BAPA | Phn-G1-(ene)₂ | (Phn)₂-EDA-G1-(ene)₂ | (Phn)₂-HDA-G1-(ene)₂ | Phn-G3-(ene)₈ | H₃PO₄ | TATATO | TMPDE | TMPSH | TEMPIC | THYTATO | TPYTATO |
|---|---|---|---|---|---|---|---|---|---|---|---|---|---|---|---|---|---|
| P3b | - | 48.2 | 39.4 | 0.3 | 7.8 | 3.9 | - | - | - | - | 0.4 | - | - | - | - | - | - |
| P4 | - | 50.1 | 37.6 | 0.3 | 7.8 | 3.2 | - | - | 1.1 | - | - | - | - | - | - | - | - |
| P5 | - | 47.5 | 38.9 | 0.3 | 7.7 | - | - | - | - | 5.5 | - | - | - | - | - | - | - |
| P6 | - | 50.5 | 37.9 | 0.3 | 7.8 | - | - | 1 | - | - | - | 2.5 | - | - | - | - | - |
| P7 | - | 70.7 | 19 | 0.4 | - | - | - | 1.2 | - | - | - | 3.2 | - | 5.4 | - | - | - |
| P8 | - | 48.2 | 39.4 | 0.3 | 7.8 | - | 1.4 | - | - | - | - | - | 2.9 | - | - | - | - |
| P1g+P9 | 21.8 | 40.3 | 24.4 | 0.3 | 4.3 | 1.9 | - | 0.3 | - | - | - | - | - | - | 4.9 | - | - |
| P10 | 22.8 | 46.1 | 19.4 | 0.3 | 1.0 | - | - | 0.6 | - | - | - | - | - | - | 7.8 | 1.8 | - |
| P11 | 25.7 | 51.7 | 8.2 | 0.4 | 1.1 | - | - | 0.6 | - | - | - | 4.4 | - | - | 8.0 | - | 2.0 |

Fig. 6

| Adhesive composite | CQ [wt%] | Irgacure 819 [wt%] | TATATO [wt%] | TEMPIC [wt%] | TPYTATO [wt%] | HA [wt%] | Glass particles [wt%] | HA (coated with Phn-G1-(ene)2) [wt%] |
|---|---|---|---|---|---|---|---|---|
| A1 | 0.1 | - | 32.1 | 67.8 | - | - | - | - |
| A2 | - | 0.5 | 14.2 | 28.4 | - | 56.8 | - | - |
| A3 | - | 0.5 | 14.2 | 28.4 | - | - | - | 56.8 |
| A4 | - | 1 | - | 80 | 19 | - | - | - |
| A5 | - | 0.9 | - | 56.4 | 13.1 | - | 29.6 | - |
| A6 | - | 1.1 | 31.8 | 67.1 | - | - | - | - |

Fig. 7

| Primer composition | Adhesive composite | Phn/Allyl | pH | Shear bond strength [MPa] |
|---|---|---|---|---|
| P1f | A2 | 0.0625 | 2.0-2.5 | 7.36 (±1.07) |
| P1g | A2 | 0.125 | 2.0-2.5 | 8.45 (±2.29) |
| P1h | A2 | 0.1875 | 2.0-2.5 | 7.41 (±1.15) |
| P1i | A2 | 0.25 | 2.0-2.5 | 4.28 (±0.65) |
| P1j | A2 | 0.5 | 2.0-2.5 | 3.46 (±1.37) |
| P1k | A2 | 1 | 2.0-2.5 | 2.44 (±0.22) |
| P2a | A2 | 0.0625 | 3.0 | 4.00 (±0.67) |
| P2b | A2 | 0.125 | 2.0-2.5 | 8.22 (±1.59) |
| P2c | A2 | 0.1875 | 2.0-2.5 | 7.67 (±1.74) |
| P2d | A2 | 0.25 | 2.0-2.5 | 4.03 (±0.73) |
| P2e | A2 | 0.5 | 2.0-2.5 | 3.77 (±0.85) |
| P3a | A2 | 0 | 4.0 | 2.90 (±0.75) |
| P3b | A2 | 0 | 2.0-2.5 | 2.97 (±0.99) |

Fig. 8

| Primer composition | Adhesive or Adhesive composite | Shear bond strength [MPa] |
|---|---|---|
| - | A1 | 0.09 (±0.07) |
| SE Bond | A1 | 0.47 (±0.04) |
| - | A2 | 0.22 (± 0.19) |
| P1g | A2 | 9.03 (±1.47) |
| P2b | A2 | 8.21 (±1.59) |
| P4 | A2 | 7.08 (±0.49) |
| P5 | A2 | 5.57 (±0.96) |
| P8 | A2 | 7.34 (±1.43) |
| P1g | A4 | 6.00 (±1.10) |
| SE Bond | SE Bond | 5.84 (±0.25) |

Fig. 9

| Pre-treatment | Primer or Adhesive | Adhesive composite | Shear bond strength [MPa] |
|---|---|---|---|
| - | P1g | A2 | 8.74 (±1.38) |
| - | P4 | A2 | 8.30 (±1.90) |
| - | P6 | A3 | 9.65 (±1.90) |
| - | P7 | A3 | 8.04 (±1.18) |
| - | Scotchbond 1 XT | Filtek Z250 | 6.36 (±0.83) |
| Etched with Phosphoric acid (35%) | Scotchbond 1 XT | Filtek Z250 | 6.03 (±1.01) |

Fig. 10

| Fixation method | Primer composition or Adhesive | Adhesive composite | Bending rigidity [Nm²] | Maximum bending moment [Nm] |
|---|---|---|---|---|
| FRAP | P1g | A2 | 0.11 (±0.01) | 1.63 (±0.66) |
| FRAP | P1g+P9 | A2 | 0.13 (±0.01) | 2.20 (±0.15) |
| K-wire 1.0 | - | - | 0.01 (±0.001) | 0.77 (±0.10) |

Fig. 11

| Substrate | Pre-treatment | Primer composition and/or Adhesive | Adhesive composite | Shear bond strength [MPa] |
|---|---|---|---|---|
| Dentin | - | P1g | A2 | 11.9 (±1.0) |
| Dentin | Etched with Phosphoric acid (35%) | Scotchbond 1 XT | Filtek Z250 | 10.3 (±1.6) |
| Enamel | - | P10 and A4 | A5 | 14.0 (±0.9) |
| Enamel | - | SE Bond Primer and SE Bond | Filtek Z250 | 5.4 (±1.1) |

Fig. 12

| Primer composition | Adhesive composite | Phn/Allyl | pH | Shear bond strength [MPa] |
|---|---|---|---|---|
| P1a | A2 | 0.00781 | 4 | 4.91 (±2.75) |
| P1b | A2 | 0.0155 | 4 | 5.62 (±1.48) |
| P1c | A2 | 0.0313 | 4 | 6.64 (±1.25) |
| P1d | A2 | 0.0625 | 3.5 | 5.60 (±2.62) |
| P1e | A2 | 0.125 | 2.0-2.5 | 2.15 (±0.67) |
| P1g | A2 | 0.125 | 2.0-2.5 | 1.47 (±0.29) |
|  | A2 | 1 | 2.0-2.5 | 0.68 (±0.49) |

Fig. 13

| Primer composition | Adhesive or Adhesive composite | Shear bond strength [MPa] |
|---|---|---|
| P1f | A6 | 5.5 (±1.1) |
| P10 | A6 | 3.9 (±1.1) |
| P1f | A4 | 9.1 (±2) |
| P10 | A4 | 11 (±2) |

Fig. 14

| Primer composition | Adhesive composite | Shear bond strength [MPa] |
|---|---|---|
| P1f | A4 | 1.3 (±0.4) |
| P10 | A4 | 5.6 (±2.0) |
| P11 | A4 | 0.6 (±0.4) |

Fig. 15

COMPOSITION COMPRISING THIOL, ALKENE AND PHOSPHONIC ACID CONTAINING COMPOUNDS FOR USE AS A PRIMER FOR ADHESION IMPROVEMENT

CROSS-REFERENCE TO RELATED APPLICATION

This application claims priority to and is a 35 U.S.C. § 371 national phase application of PCT/EP2018/079289 (WO2019/081641), filed on Oct. 25, 2018 entitled "A COMPOSITION COMPRISING THIOL, ALKENE AND PHOSPHONIC ACID CONTAINING COMPOUNDS FOR USE AS A PRIMER FOR ADHESION IMPROVEMENT", which application claims priority to and the benefit of PCT/EP2017/077350, filed October 25, 2017, the disclosures of which are incorporated herein by reference in their entirety.

FIELD OF THE INVENTION

The present invention relates to a composition that may be used as a primer on bone or tooth. The primer composition provides good mechanical properties and may be applied also to wet bone. The invention further relates to an allyl-phosphonic acid containing compound. The present invention may be used in various applications and may be provided as a kit.

BACKGROUND

With an increasing number of elderly people in the next decades it is estimated that the number of fractures all categories will increase substantially. Most fractures in the society are caused by accidents while a smaller amount is caused by diseases such as osteoporosis. Among the accidental factors including traffic, fall, leisure and violence, fractures due to fall is the most common causes. In Sweden statistics showed that fractures all categories was the most frequent cause to in-hospital treatment among people aged 65+. Within the next decades it can be foreseen that the pattern of fractures is similar all around the world as the demographic picture is the same in most countries. As a consequence, the health care costs will increase tremendously due to the need of in-hospital treatment. Thus, there is a need for the society to focus not only on primary prevention but also on new and effective fracture treatment aiming at reducing the number of fractures and the total in-hospital stay. The treatment of fractures all categories are conservative with no surgical procedures or with surgical stabilization with various tools. The most frequent surgical method is stabilizing the fractures by application of metals and screws made of titanium or stainless steel. Depending on the type and localization of the fractures, the surgical procedure is performed during either local or general anesthesiology. Although the accurate and good surgical results including fracture stabilization and healing, there is a demand for alternative material use.

For decades, researchers have focused on developing adhesive systems for bone fracture fixation and various approaches have been evaluated. However, the struggle with either poor adhesion or biocompatibility issues of the today available adhesive systems have delayed an expansion of the usage area further than the current use of bone cements. Recent research has come a long way in providing solutions for adhesive systems for wet environments with more biocompatible approaches and innovative methods. One promising fixation method is the Fiber Reinforced Adhesive Patch (FRAP), described in WO2011048077. The FRAP is applied over the fracture without entering the cross-section of the break, thus diminishing the interference with the healing of the fracture compared to other proposed adhesive fixation methods. The FRAP technology can enable a quick and mild fixation of various fractures that today are considered difficult due to sensitive locations, near joints or when drilling is not a possible option.

To tackle the difficulty in adhering to wet surfaces and then stay stable in the wet environment, the adhesive system may contain an adhesion-enhancing primer solution and a more hydrophobic adhesive matrix of the triazine-trione components tris[2-(3-mercaptopropionyloxy)ethyl] isocyanurate (TEMPIC) and 1,3,5-Triallyl-1,3,5-triazine-2,4,6(1H, 3H,5H)-trione (TATATO). According to earlier studies, the adhesion-enhancing primer is very important for the final adhesive strength towards wet bone. The primer should both adhere to the wet bone surface and create a compatible surface and preferably have the capacity to covalently bond to the adhesive matrix. This approach has been used in dentistry for many years, where the use of acrylate monomers with acidic adhesion-enhancing groups of phosphoric, phosphonic or carboxylic acid have enabled self-etch adhesive systems. The acidic monomers dissolve hydroxyapatite and create ionic bonds to calcium ions forming precipitates with very low solubility that integrate within the hydroxyapatite surface. However, the use of acrylate polymerization systems is connected to cytotoxic leakage of unreacted monomers. Still, the use of such adhesion-enhancing groups is of high interest for bone adhesives due to the large fraction of hydroxyapatite in bone.

WO2012126695 discloses a stable curable thiol-ene composition suitable for preparing three dimensional objects. WO2012126695 aims at solving the problem of poor shelf life of curable thiol-ene compositions and discloses a composition comprising an ethylenically or acetylenically unsaturated monomer, a thiol, optionally a photoinitiator, a phosphonic acid and a component of benzene or naphthalene containing compound.

Adhesive systems for fixation of bone fractures are much needed as an alternative or complement to pins or screws for bone fractures. However, the wet environment in the body is challenging and many approaches struggle with either poor adhesion, biocompatibility issues or an inadequate fixation methodology. This has delayed an expansion of the clinical applications of adhesives for bone fractures.

SUMMARY OF THE INVENTION

The object of the present invention is to overcome the drawbacks of the prior art. The present primers enable a high strength adhesive fixation method functioning in the wet environment present such as in bone repair applications. For dental restoratives, our primer could be vital for being able to implement use of thiol-ene resins which could reduce problems of leakage of monomers and curing shrinkage stress of today's acrylate resins. Thiol-ene resins would also distance dental restorations from use of bisphenol A derivatives which are known to be potentially harmful (as is monomer leakage e.g. from acrylates).

The present invention uses thiol-ene coupling polymerization and enables the use of thiol-ene resins in both bone and dental restorations. Thiol-ene resins have the benefits of being prepared through a benign and efficient reaction, insensitive to oxygen inhibition. Thiol-ene resins gelate at high conversions due to a stepwise network formation of flexible thioether linkages. A high gelation point reduces the curing induced shrinkage and increases the final conversion of the crosslinked network, which could lead to both better stability and minimal release of monomers from the restorations, compared to acrylate systems that today are used both as dental restoratives and bone cements.

Aspects

In a first aspect the present invention relates to composition according to claim 1.

In a second aspect the present invention relates to the use of the composition according to the present invention as a primer for hard tissue such as bone or tooth, or metal or synthetic material.

In a third aspect the present invention relates to the use of the composition according to the present invention as a coating or a filler for hard tissue, or metal or synthetic material.

In a fourth aspect the present invention relates to a patch comprising
- a first layer, also called primer, comprising the composition according to any one of claims 1 to 23;
- a second layer of adhesive comprising photoinitiator, a Component A comprising at least two thiol groups, a Component B comprising vinyl reactive groups chosen from vinyl, acrylate, methacrylate, allyl and unsaturated cyclic vinyls, or alkynes and optionally fillers; and
- Optionally a third layer comprising Component A comprising at least two thiol groups, a Component B comprising vinyl reactive groups chosen from vinyl, acrylate, methacrylate, allyl and unsaturated cyclic vinyls, or alkynes and fillers.

In a fifth aspect the present invention relates to a filler comprising the composition according to the present invention wherein the filler further comprises particles of a ceramic filler, such as a calcium phosphate, e.g. hydroxyapatite.

In an sixth aspect the present invention relates to a ceramic material, such as a calcium phosphate material, having a coating comprising the composition according to the present invention.

In a seventh aspect the present invention relates to a kit comprising at least two containers wherein
any one container in the kit can contain any of
water;
a first compound having at least two thiol groups;
a second compound having the general structure of

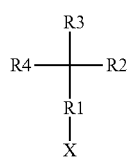

wherein R1 is an alkyl, a dialkyl ether, dialkyl ester, dialkyl urethane or a dialkyl amide group, R2 is an at least one allyl or alkyne containing group, R3 is hydrogen, an alkyl group or an at least one allyl containing group, or an alkyne group or an at least one alkyne containing group, and R4 is hydrogen, an alkyl group or an at least one allyl containing group, or an alkyne group or an at least one alkyne containing group;
wherein the first compound or the second compound comprises at least one phosphonic acid containing group X with proviso that when the second compound comprises the at least one phosphonic acid containing group said group is bound to the R1 group;
and a photo initiator;
wherein the molar ratio between the phosphonic acid groups and the allyl groups or the thiol groups in the composition is 0.01 to 4

Various Embodiments of the Invention

An aqueous composition comprising
a first compound having at least two thiol groups;
a second compound having the general structure of

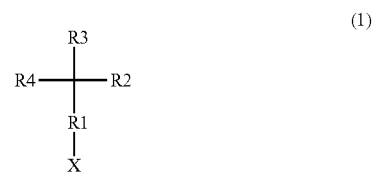

wherein R1 is an alkyl, a dialkyl ether, dialkyl ester, dialkyl urethane or a dialkyl amide group, R2 is an at least one allyl or alkyne containing group, R3 is hydrogen, an alkyl group or an at least one allyl containing group, or an alkyne group or an at least one alkyne containing group, and R4 is hydrogen, an alkyl group or an at least one allyl containing group, or an alkyne group or an at least one alkyne containing group;
wherein the first compound or the second compound comprises at least one phosphonic acid containing group X with the proviso that when the second compound comprises the at least one phosphonic acid containing group said group is bound to the R1 group; and
a third compound or additional compounds comprising at least one alkyne containing group;
a photo initiator.

The aqueous composition wherein the pH of the composition is in the range of 1.5 to 4.

The aqueous composition, wherein the molar ratio between the phosphonic acid groups and the allyles groups in the composition is 0.01 to 4 with alkynes as the third compound.

The aqueous composition according to claim wherein the molar ratio between the phosphonic acid groups and the allyl groups is 0.01-3 or 0.01-2 or 0.01-1 or 0.01 to 0.1 or 0.03 to 0.3 or 0.04 to 0.25 or 0.06 to 0.2 with alkynes as the third compound.

The aqueous composition wherein the molar ratio between the phosphonic acid groups and the allyl groups is 0.01 to 0.1 with alkynes as the third compound.

The aqueous composition wherein the molar ratio between the phosphonic acid groups and the thiols groups is 0.01 to 0.5 with alkynes as the third compound.

The aqueous composition wherein the molar ratio between the phosphonic acid groups and the alkyne groups is 0.02 to 1 with alkynes as third compound or as second and third compounds.

The aqueous composition wherein the molar ratio between the alkene and/or allyl groups and alkyne groups is 0.02 to 2 with alkynes as third compound.

The aqueous composition wherein R1 is a C1-C10 alkyl group such as a C1-C6 alkyl group and wherein R2 is an alkyl allyl group or an alkoxy allyl group or alkyl alkyne group or an alkoxy alkyne group.

The aqueous composition wherein the second compound has the general structure (1) and wherein X is a phosphonic acid group.

The aqueous composition wherein each of the at least one allyl containing group is an alkyl allyl group containing two or more allyl groups, or each of the at least one alkyne containing group is an alkyl alkyne group containing one or more alkyne groups, or each of the at least one allyl containing group is a dialkyl ether allyl group containing two or more allyl groups or each of the at least one alkyne containing group is a dialkyl ether alkyne group containing one or more alkyne groups.

The aqueous composition wherein the second compound is a dendrimer having four or more allyl groups or two or more alkyne groups.

The aqueous composition wherein the third compound or additional compounds is a dendrimer having two or more alkyne groups.

The aqueous composition wherein the phosphonic acid containing group of the second compound has the structure of:

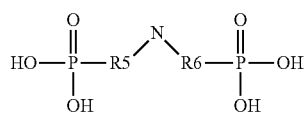

(3)

wherein R5 and R6 are individually an alkyl group such as a C1-C10 alkyl groups such as a methylene or an ethylene group.

The aqueous composition wherein the second compound comprises at least one phosphonic acid containing group and wherein the composition comprises a third compound having the general structure of

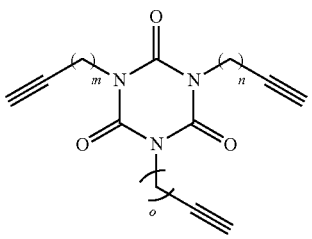

wherein m, n and o is 1 or higher.

The aqueous composition wherein the photo initiator is selected from lithium phenyl(2,4,6-trimethylbenzoyl)phosphinate (LAP), Irgacure 819, (2,4,6-trimethylbenzoyl)-phosphine oxide (BAPO), diphenyl(2,4,6-trimethylbenzoyl) phosphine oxide (TPO), camphorquinone, carboxylated camphorquinone.

The aqueous composition wherein the first compound is selected from tris 2-(3-mercaptopropionyloxy) ethyl isocyanurate (TEMPIC), ethoxylated-trimethylolpropane tri-3-mercaptopropionate (ETTMP), trimethylolpropane tri-3-mercaptopropionate, thiolated poly(ethylene glycol), 1,3,5-tris(3-mercaptopropyl)-1,3,5-triazinane-2,4,6-trione (TTTSH) and ethoxylated-trimethylolpropane tri-thiol (ETTT) and thiolated multi armed poly(ethylene glycol).

The aqueous composition wherein the composition further comprises ethanol or acetone preferably in an amount of 10-90 wt % such as 40-60 wt % of the total weight of the composition.

The aqueous composition wherein the composition comprises a third compound selected from 1,3,5-tri(prop-2-yn-1-yl)-1,3,5-triazinane-2,4,6-trione (TPYTATO), 1,3,5-tri(hex-5-yn-1-yl)-1,3,5-triazinane-2,4,6-trione (THYTATO), Bis(propynyloxymethyl)propanoic acid (BPPA).

The aqueous composition wherein the second compound has the general structure of

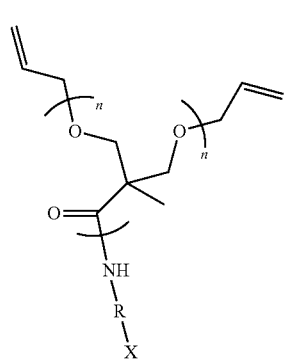

(5)

wherein n is 1 or higher, R is an alkyl group and X is a phosphonic acid containing group.

The aqueous composition wherein the total amount of the second compound and third compound is 1-10 wt %, such as 2-6 wt %, or 4-5 wt %.

The aqueous composition further comprising a fourth compound or additional compounds comprising at least one allyl containing group or at least one thiol containing group or at least one alkyne.

The aqueous composition wherein the second compound comprises alkyl groups comprising alkene containing groups.

The use of the composition as a primer for hard tissue such as bone or tooth, or for a metal or synthetic material.

The use of the composition as a coating or a filler for hard tissue, or for a metal or synthetic material.

A patch comprising
  a first layer (also called primer layer) comprising the composition according to the present invention;
  a second layer of adhesive comprising photoinitiator, a Component A comprising at least two thiol groups, a Component B comprising vinyl reactive groups chosen from vinyl, acrylate, methacrylate, allyl and unsaturated cyclic vinyls, or alkynes; and
  Optionally a third layer comprising Component A comprising at least two thiol groups, a Component B comprising vinyl reactive groups chosen from vinyl, acrylate, methacrylate, allyl and unsaturated cyclic vinyls, or alkynes.

The patch comprising a filler.

The patch wherein the filler is a ceramic filler.

The patch wherein the ceramic filler is in the third layer.

The patch according to claim 25 wherein the composition provided on the primer layer further comprises fibres.

A filler comprising the composition wherein the filler further comprises particles of a cermic filler material, such as calcium phosphate, e.g. hydroxyapatite.

A calcium phosphate material having a coating comprising the composition according to the present invention.

A kit comprising at least two containers wherein
  any one container in the kit can contain any of water;
  a first compound having at least two thiol groups;

a second compound having the general structure of

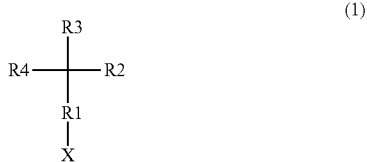

wherein R1 is an alkyl, a dialkyl ether, dialkyl ester, dialkyl urethane or a dialkyl amide group, R2 is an at least one allyl or alkyne containing group, R3 is hydrogen, an alkyl group or an at least one allyl containing group, or an alkyne group or an at least one alkyne containing group, and R4 is hydrogen, an alkyl group or an at least one allyl containing group, or an alkyne group or an at least one alkyne containing group;

wherein the first compound or the second compound comprises at least one phosphonic acid containing group X with proviso that when the second compound comprises the at least one phosphonic acid containing group said group is bound to the R1 group;

a third compound or additional compounds comprising at least one alkyne containing group;

and a photo initiator.

The kit wherein the kit is in the form of an at least two compartment syringe.

The kit wherein the kit comprises at least two additional containers wherein any one container in the kit can contain any of a photo initiator, a Component A comprising at least two thiol groups, a Component B comprising vinyl reactive groups chosen from vinyl, acrylate, methacrylate, allyl and unsaturated cyclic vinyls, or alkynes and optionally calcium phosphate particles or functionalized calcium phosphate particles; with proviso that the Compound A is not present in the same container as the Compound B.

The kit wherein the kit comprises calcium phosphate particles or functionalized calcium phosphate particles.

All the embodiments described herein relates to all the aspects unless otherwise stated.

BRIEF DESCRIPTION OF THE FIGURES

FIG. 6 shows a table of primer compositions. Molecular structures are shown in FIGS. 1-4.

FIG. 7 shows a table of adhesive compositions.

FIG. 8 shows a table of shear bond strength of primer and adhesive composite exhibiting different phosphonic acid/allyl ratios and pH. FRAP on bone is disclosed.

FIG. 9 shows a table of shear bond strength of primer and adhesive composite. FRAP on bone is disclosed.

FIG. 10 shows a table of shear bond strength of the present invention and pre-treatment. Adhesive on bone is disclosed.

FIG. 11 shows mechanical properties of fixation methods. FRAP fixation of phalangeal fracture model is disclosed.

FIG. 12 shows shear bond strength of pre-treatment and the primer and adhesive composite. Adhesive on dentin is disclosed.

FIG. 13 shows a table of shear bond strength of primer and adhesive composite exhibiting different phosphonic acid/allyl ratios and pH. Adhesive on steel is disclosed.

FIG. 14 shows a table of shear bond strength of primer and adhesive on porcine metacarpal comparing thiol-ene and thiol-yne compositions.

FIG. 15 shows a table of shear bond strength of primer and adhesive on bone contaminated with dried blood serum.

DETAILED DESCRIPTION OF THE INVENTION

Figure 1:
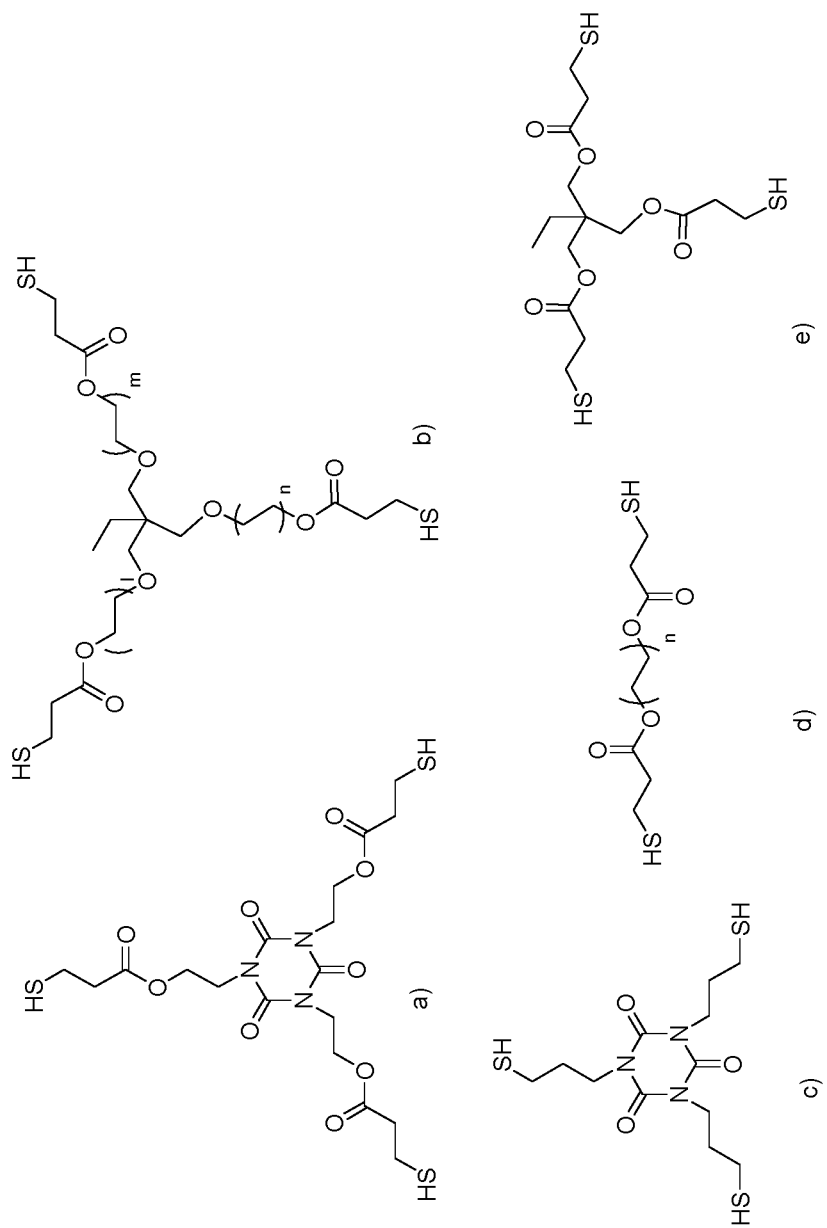
FIG. 1 shows the structure of molecules suitable as the first compound in the primer composition: a) Tris[2-(3-mercaptopropionyloxy)ethyl] isocyanurate, TEMPIC; b) Ethoxylated-Trimethylolpropan Tri(3-Mercaptopropionate), ETTMP; c) 1,3,5-tris(3-mercaptopropyl)-1,3,5-triazinane-2,4,6-trione, TTTSH; d) thiolated poly(ethylene glycol); e) Trimethylolpropane Tri(3-mercaptopropionate), TMPMP.

The present inventors have shown that one of the most important components in fixation of tissue and material/patch adherence to tissue is a primer that increases the bond strength between the substrate and the tissue for example bone. The present invention is connected to the development of a Fiber Reinforced Adhesive Patch (FRAP)—a novel concept for adhesive fixation of bone fractures that could provide a new and innovative way of treating bone fractures and defects in a range of applications. The FRAP is further described in WO2011048077 and the present invention may be used in combination with the FRAP.

Until now the bond strength between a substrate and the tissue has not been sufficient for many applications such as bone restoration or fracture fixation. However the present inventors have developed new high performance primer components and primer compositions. These could solve the critical problem of getting high enough adhesion to tissue especially bone. Moreover, the primers also have additional applications (besides the FRAP concept) such as in other bone repair applications or void filling applications where adhesives need to be used and in dental applications where a major opportunity could exist in being able to improve the adhesion to tooth of dental repairs.

The concept is based on years' of research into the materials and their manufacturing. Mechanical shear tests and 3-point bending tests display that the primer can provide competing bond strength to today's dental adhesives towards both bone and tooth. The present primers enable superior phalangeal fracture fixations (compared to Kirschner wires) and can even compete with screw fixated metal plates. As an example we have benchmarked against the commercially available dental adhesive SE Bond which noted shear strength of 5.84 MPa on wet bone substrates.

Many commercially available dental primers or fixation compositions contains acrylates which from a toxicological point of view is not wanted. The present primers have shown unexpectedly high mechanical strength and the primers have shown high biocompatibility.

The Composition

The composition according to the present invention is an aqueous composition comprising a first compound having at least two thiol groups and a second compound having the general structure of

(1)

wherein R1 is an alkyl, a dialkyl ether, dialkyl ester, dialkyl urethane or a dialkyl amide group, R2 is an at least one allyl or alkyne containing group, R3 is hydrogen, an alkyl group or an at least one allyl containing group, or an alkyne group or an at least one alkyne containing group, and R4 is hydrogen, an alkyl group or an at least one allyl containing group, or an alkyne group or an at least one alkyne containing group. The alkyl groups of the second compound may comprise unsaturations in the form of an alkene, allyle and alkyne containing group, i.e. unsaturations inside (alkenes and alkynes) and at the end of the compounds (allyles and alkynes). In one embodiment, the compounds comprise unsaturations only at the end of the compounds. In another embodiment, the compounds comprise only unsaturations only inside the compounds. In a further embodiment, the compounds comprise a mix of unsaturations inside and at the end of the compounds. Furthermore the first compound or the second compound comprises at least one phosphonic acid containing group. This group when arranged on the second compound is bound to the R1 group of the general structure (1). The composition further comprises a photo initiator. The photo initiator may in an alternative embodiment be present in the adhesive composition. In one embodiment, the composition comprises a third compound or additional compounds comprising at least one allyl containing group or at least one thiol group or at least one alkyne containing group. In one embodiment, the third or additional compounds may be present in the primer composition. In another embodiment one or more of the third or additional compounds may be present in the adhesive composition.

The alkene groups used,

Each alkyne can react with two thiols and may thus increase the crosslinking density that leads to a stronger network compared to using allyl groups. The general ratio of phosphonic acid to allyl (alkene) is 0.01-4 with alkynes as the third compound. The following ratios are presently the preferred ones:

Phosphonic acid to allyl (alkene) of 0.01-1 with alkynes as the third compound;

Phosphonic acid to thiol of 0.01-0.5 with alkynes as the third compound;

Phosphonic acid to alkyne of 0.02-1 with alkynes as the third compound;

Phosphonic acid to alkyne of 0.02-1 with alkynes as the second and third compounds;

Alkene and/or allyl to alkyne 0.02-2 with alkynes as the third compound;

For metal substrates, molar ratios between phosphonic acid and allyls may also be 0.005 to 0.1 or 0.01 to 0.1.

For metal substrates, molar ratios between phosphonic acid and thiols may also be 0.005 to 0.1 or 0.01 to 0.1.

For metal substrates molar, ratios between phosphonic acid and alkynes may also be 0.01 to 0.1 or 0.01 to 0.1.

By varying the third compound, the number of allyl groups and alkyne groups may be in a molar ratio of 0.01 to 10 such as 0.02 to 5 or 0.02 to 2, such as 0.06 to 0.4 or 0.06 to 0.25. By using alkynes as the third compound the molar ratio of phosphonic acid groups and alkyne groups may be 0.01 to 1, such as 0.02 to 0.2. If alkynes are used as the second and third compound, the molar ratio between phosphonic acid groups and alkyne groups may be 0.01 to 1, such as 0.01 to 0.2 By having alkynes as the third and alternatively the second compound, the molar ratio between thiol groups and phosphonic acid groups may be 0.01 to 0.5, such as 0.01 to 0.3.

If alkynes are used as the second and the third compound, without allyl groups or other alkenes in the composition, the molar ratio between phosphonic acid groups and alkyne groups may be 0.01 to 1 such as 0.01 to 0.2 By having alkynes as the third, and alternatively the second compound, without allyls or other alkenes the molar ratio between thiol groups and phosphonic acid groups may be 0.01 to 0.5 such as 0.01 to 0.3.

Also the first, second and third or additional compounds are preferably at least partly soluble in water.

By varying the number of allyl groups and phosphonic acid groups on the first, second and the optional third or additional compounds the molar ratio between said functional groups may be varied and thereby the shear bond strength may be improved. The molar ratio may be varied by adding the different compounds in various amounts and/or by using compounds having multiple allyl groups or phosphonic acid groups. For example, by using a second or third compounds or additional compounds having a dendritic structure with alkyne containing groups. The molar ratio between the phosphonic acid groups and the allyl groups may be 0.01 to 4, e.g 0.01-3, 0.01-2, or 0.01-1, such as 0.01 to 0.1 or, 0.03 to 0.3 such as 0.04 to 0.25, or 0.06 to 0.20.

The ratio of the amount of phosphonic acid groups and the reactive groups for thiol-ene coupling was found to be a major factor in order to improve the bond strength to bone or metal. Phosphonic acid molecules are known to promote good bond strength to dentin and enamel when they are used in vinyl resins. However, phosphonic acid molecules are also well known radical scavengers, especially for thiyl (also named sulfenyl) radicals and are i.e. used as inhibitors in the thiol-ene resins disclosed in WO2012126695 and are supposed to work well even in amounts of 0.01 wt %. In thiol-ene polymerization, it is important to yield high conversion to obtain a mechanically robust material and high bond strength and thus any radical scavenging effect is detrimental for achieving high bond strength with thiol-ene resins or thiol-yne resins. Allyls and alkenes reacts similarly to thiols with the main difference that an allyl only can react with one thiol and an alkyne can react with two thiols. Thus an unpredictably large increase in bond strength was obtained when certain allyls was replaced with alkynes in the primer as well, with an increased bond strength from 0.6

MPa for the P11 primer with only allyls as unsaturations to 5.6 MPa when the corresponding primer P10 with most allyl monomers replaced with an alkyne monomer was used on blood serum contaminated bone surface. An increase in bond strength from 9.1 MPa to 11 MPa was also seen when the alkyne containing primer P10 was used together with the thiol-yne adhesive composition A4 compared to using the P1f primer.

The first compound may be any suitable dithiol containing compound. The first compound may comprise at least three thiol groups, or at least four thiol groups. In FIG. 1 non-limiting examples of suitable first compounds are disclosed. In one embodiment the first compound is selected from tris 2-(3-mercaptopropionyloxy)ethyl isocyanurate (TEMPIC), ethoxylated-trimethylolpropane tri-3-mercaptopropionate (ETTMP), trimethylolpropane tri-3-mercaptopropionate (TMPMP), thiolated poly(ethylene glycol), 1,3,5-tris(3-mercaptopropyl)-1,3,5-triazinane-2,4,6-trione (TTTSH) and ethoxylated-trimethylolpropane tri-thiol (ETTT) and thiolated multi armed poly(ethylene glycol). In another embodiment the first compound is ETTMP. In one embodiment the amount of the first compound is 1 to 15 wt % such as 3 to 12 wt %, or 5 to 10 wt % of the total composition.

The second compound may be any suitable allyl containing compound having the general structure (1). R1 may be a C1-C10 alkyl group such as a C1-C6 alkyl group. R2 may contain at least two allyl groups, or at least three, or at least 4 allyl groups or at least one alkyne groups, or at least two, or at least three, or at least 4 alkyne groups. In one embodiment R2 is an alkyl allyl group or an alkoxy allyl group, or an alkyl alkyne group or an alkoxy alkyne group. In another embodiment each of the at least one allyl containing group is an alkyl allyl group containing two or more allyl groups or each of the at least one alkyne containing group is an alkyl alkyne group containing one or more alkyne groups, or each of the at least one alkyne containing group is an alkyl alkyne group containing one or more alkyne groups, or each of the at least one allyl containing group is a dialkyl ether allyl group containing two or more allyl groups or each of the at least one alkyne containing group is a dialkyl ether alkyne group containing one or more alkyne groups. R3 may be a hydrogen, an alkyl group or an at least one allyl containing group or an alkyne group or an at least one alkyne containing group. In one embodiment R3 is an alkyl group such as a methyl group. In another embodiment R3 is an alkyl allyl group or an alkoxy allyl group or an alkyl alkyne group or an alkoxy alkyne group. In one embodiment R3 is an at least one allyl containing group containing two or more allyl groups or an at least one alkyne containing group containing one or more alkyne groups. R4 may be a hydrogen, an alkyl group or an at least one allyl containing group or an at least one allyl containing group. In one embodiment R4 is an alkyl group such as a methyl group. In another embodiment R4 is an alkyl allyl group or an alkoxy allyl group or an alkyl alkyne group or an alkoxy alkyne group. In one embodiment R4 is an at least one allyl containing group containing two or more allyl groups or an at least one alkyne containing group containing one or more alkyne groups. In one embodiment the second compound is a dendrimer having four or more allyl groups or two or more alkyne groups.

The second compound may comprise at least one phosphonic acid group and it is bound to the R1 group of the general structure (1). In one embodiment the second compound comprises two or more phosphonic acid groups. In one embodiment the phosphonic acid containing group of the second compound has the structure of:

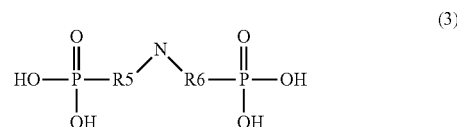

wherein R5 and R6 are individually an alkyl group such as a C1-C10 alkyl groups such as a methylene or an ethylene group.

Figure 2:
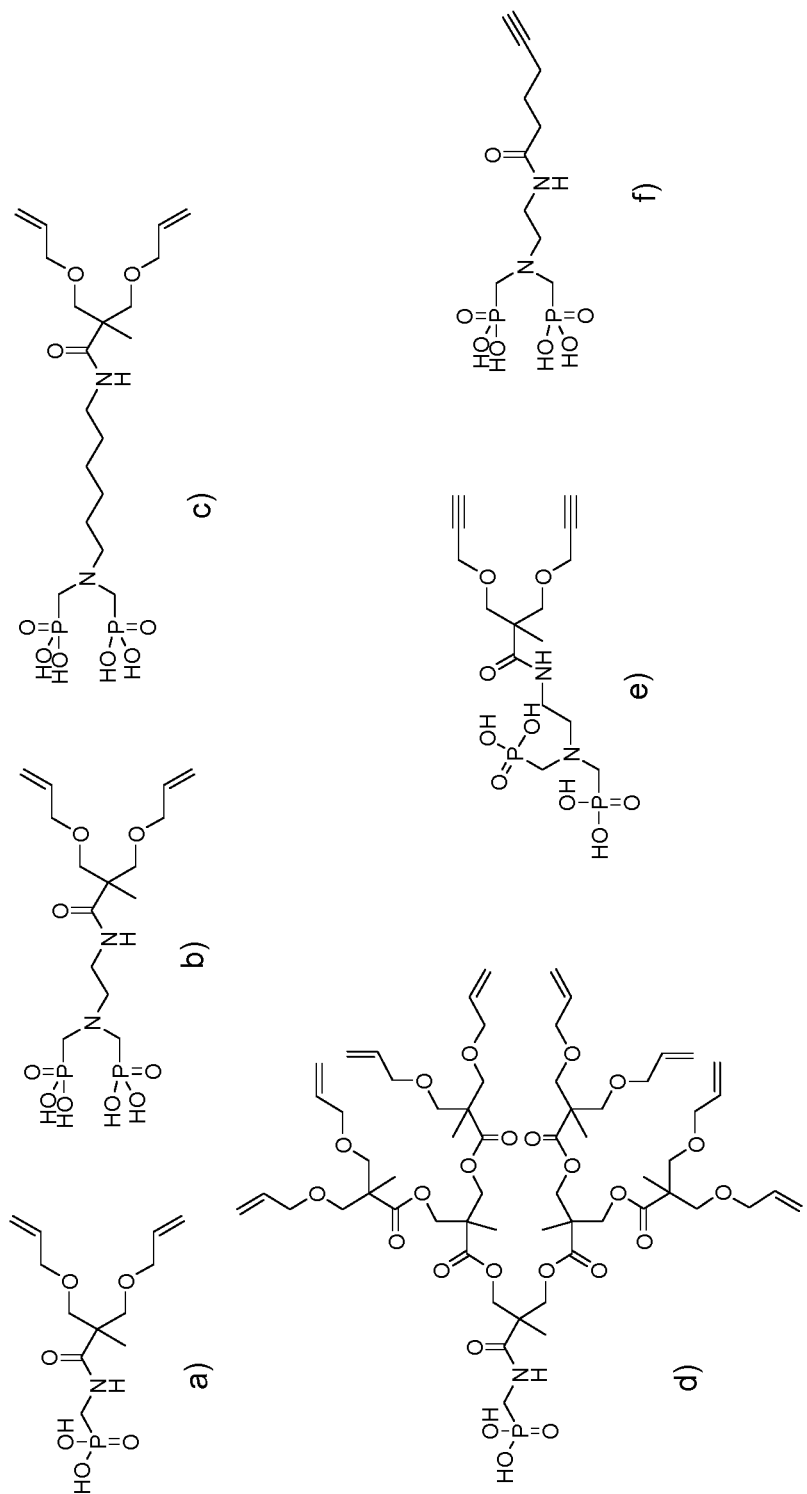
FIG. 2 illustrates some examples of dendritic molecules suitable as the second compound in the primer composition: a) Bis(allyloxymethyl)methylpropanamido)methyl) phosphonic acid, Phn-G1-(ene)$_2$, b) Bis(allyloxymethyl)methylpropanamido)ethyl) azanediyl)bis(methylene))bis(phosphonic acid), (Phn)$_2$-EDA-G1-(ene)$_2$, c) (((6-bis(allyloxymethyl)methylpropanamido)hexyl) azanediyl)bis(methylene))bis(phosphonic acid), (Phn)$_2$-HDA-G1-(ene)$_2$, d) Phn-G3-(ene)$_8$. e) (((2-(2-methyl-3-(prop-2-yn-1-yloxy)-2-((prop-2-yn-1-yloxy)methyl)propanamido)ethyl) azanediyl)bis(methylene))bis(phosphonic acid), (Phn)$_2$-EDA-G1-yne, f) (((2-(hex-5-ynamido)ethyl)azanediyl)bis(methylene))bis(phosphonic acid), (Phn)$_2$-EDA-G0-yne.

In one embodiment the second compound is selected from the compounds disclosed in FIG. 2, a) Bis(allyloxymethyl)methylpropanamido)methyl) phosphonic acid, Phn-G1-(ene)$_2$, b) Bis(allyloxymethyl)methylpropanamido)ethyl) azanediyl)bis(methylene))bis(phosphonic acid), (Phn)$_2$-EDA-G1-(ene)$_2$, c) (((6-bis(allyloxymethyl)methylpropanamido)hexyl) azanediyl)bis(methylene))bis(phosphonic acid), (Phn)$_2$-HDA-G1-(ene)$_2$, d) Phn-G3-(ene)$_8$. e) (((2-(2-methyl-3-(prop-2-yn-1-yloxy)-2-((prop-2-yn-1-yloxy)methyl)propanamido)ethyl)azanediyl)bis(methylene))bis(phosphonic acid), (Phn)$_2$-EDA-G1-yne, f) (((2-(hex-5-ynamido)ethyl)azanediyl)bis(methylene))bis(phosphonic acid), (Phn)$_2$-EDA-G0-yne.

In one embodiment the amount of the second compound is 0.1 to 15 wt % such as 1 to 10 wt %, or 2 to 8 wt %, or 3 to 5 wt % of the total composition. In one embodiment the amount of the second compound is 0.5 to 2.5 wt %.

The third compound comprises at least one alkyne containing group. The third compound may have the general structure of

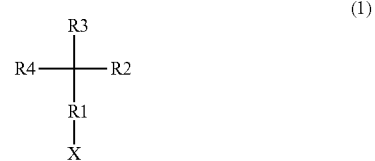

wherein R1 is an alkyl, a dialkyl ether, dialkyl ester, dialkyl urethane or a dialkyl amide group, R2 is an at least one allyl containing group or an at least one alkyne containing group, R3 is hydrogen, an alkyl group or an at least one allyl containing group or an at least one alkyne containing group and R4 is hydrogen, an alkyl group or an at least one allyl containing group or an at least one alkyne containing group. R1 may be a C1-C10 alkyl group such as a C1-C6 alkyl group. R2 may contain at least two allyl groups, or at least three, or at least 4 allyl groups or at least two alkyne groups, or at least three, or at least 4 alkyne groups. In one embodiment R2 is an alkyl allyl group or an alkoxy allyl group or an alkyl alkyne group or an alkoxy alkyne group. In another embodiment each of the at least one allyl containing group is an alkyl allyl group containing two or more allyl groups or each of the at least one alkyne containing group is an alkyl alkyne group containing one or more alkyne groups, or wherein each of the at least one allyl containing group is a dialkyl ether allyl group containing two or more allyl groups or each of the at least one alkyne containing group is a dialkyl ether alkyne group containing one or more alkyne groups. R3 may be a hydrogen, an alkyl group or an at least one allyl containing group or an at least one alkyne containing group. In one embodiment R3 is an alkyl group such as a methyl group. In another embodiment R3 is an alkyl allyl group or an alkoxy allyl group or an alkyl alkyne group or an alkoxy alkyne group. In one embodiment R3 is an at least one allyl containing group containing two or more allyl groups or an at least one alkyne containing group containing one or more alkyne groups. R4 may be a hydrogen, an alkyl group or an at least one allyl containing group or an at least one alkyne containing group. In one embodiment R4 is an alkyl group such as a methyl group. In another embodiment R4 is an alkyl allyl group or an alkoxy allyl group or an alkyl alkyne group or an alkoxy alkyne group. In one embodiment R4 is an at least one allyl containing group containing two or more allyl groups or an at least one alkyne containing group containing one or more alkyne groups.

In one embodiment the third compound has the general structure of

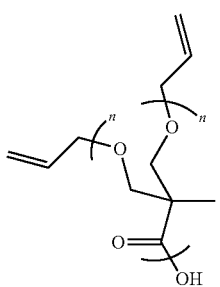

(4)

wherein n is 1 or higher. In one embodiment the third compound or additional compounds is/are a dendrimer having four or more allyl groups or two or more alkyne groups.

In one embodiment, the second compound comprises at least one phosphonic acid containing group and wherein the composition comprises a third compound having the general structure of

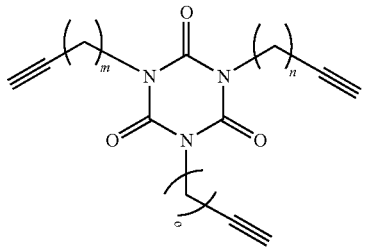

wherein m, n and o is 1 or higher.

Figure 3:
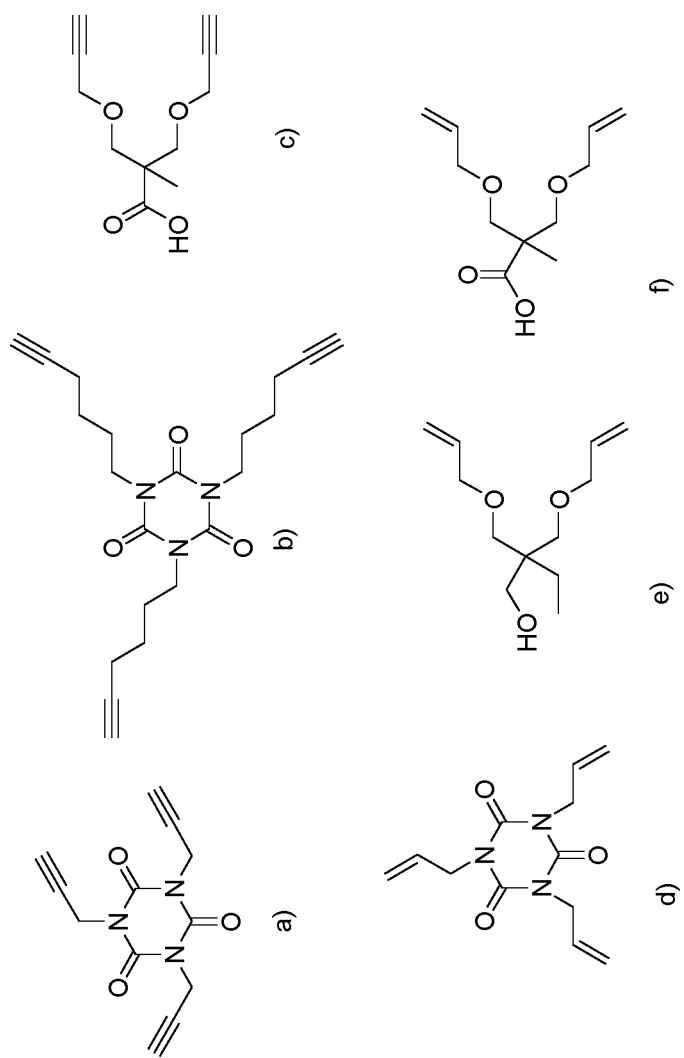
FIG. 3 illustrates some examples of molecules suitable as the third compound or additional compounds in the primer composition: a) 1,3,5-tri(prop-2-yn-1-yl)-1,3,5-triazinane-2,4,6-trione (TPYTATO), b) 1,3,5-tri(hex-5-yn-1-yl)-1,3,5-triazinane-2,4,6-trione (THYTATO), c) Bis(propynyloxymethyl)propanoic acid (BPPA), d) 1,3,5-Triallyl-1,3,5-triazine-2,4,6(1H,3H,5H)-trione, TATATO; e) Trimethylolpropane diallyl ether (TMPDE); and f) Bis(allyloxymethyl)propanoic acid, BAPA.

In one embodiment the third or additional compounds is the same compound as the second compound without the at least one phosphonic acid group. In one embodiment the third compound is selected from 1,3,5-tri(prop-2-yn-1-yl)-1,3,5-triazinane-2,4,6-trione (TPYTATO), 1,3,5-tri(hex-5-yn-1-yl)-1,3,5-triazinane-2,4,6-trione (THYTATO), Bis(propynyloxymethyl)propanoic acid (BPPA), 1,3,5-triallyl-1,3,5-triazine-2,4,6-trione (TATATO), trimethylolpropane diallyl ether (TMPDE) and bis(allyloxymethyl)propionic acid (BAPA), FIG. 3. In one embodiment the amount of the third compound is 1 to 10 wt % of the total composition, such as 2 to 7 wt % or 3 to 5 wt %. The amount is partly dependent on the wanted ratio between the phosphonic acid groups and allyl groups.

The total amount of allyl compounds in the composition is preferably 0.1 to 10 wt %. The total amount of allyl compounds is the amount of the second compound. In exemplary embodiments, the total amount of allyl compounds is 0.1 wt % or more, or 1 wt % or more, or 2 wt % or more, or 3 wt % or more, or 4 wt % or more, but less than 10 wt %, or 9 wt % or less, or 8 wt % or less, or 7 wt % or less, or 6 wt % or less, or 5 wt % or less. In one embodiment the total amount of allyl compounds in the composition is around 4.5 wt %.

The total amount of alkyne compounds in the composition is preferably 0.1 to 10 wt %. The total amount of alkyne compounds is the amount of the second and third compounds. In exemplary embodiments, the total amount of alkyne compounds is 0.1 wt % or more, or 1 wt % or more, or 2 wt % or more, or 3 wt % or more, or 4 wt % or more, but less than 10 wt %, or 9 wt % or less, or 8 wt % or less, or 7 wt % or less, or 6 wt % or less, or 5 wt % or less. In one embodiment the total amount of alkyne compounds in the composition is around 4.5 wt %.

Figure 4:
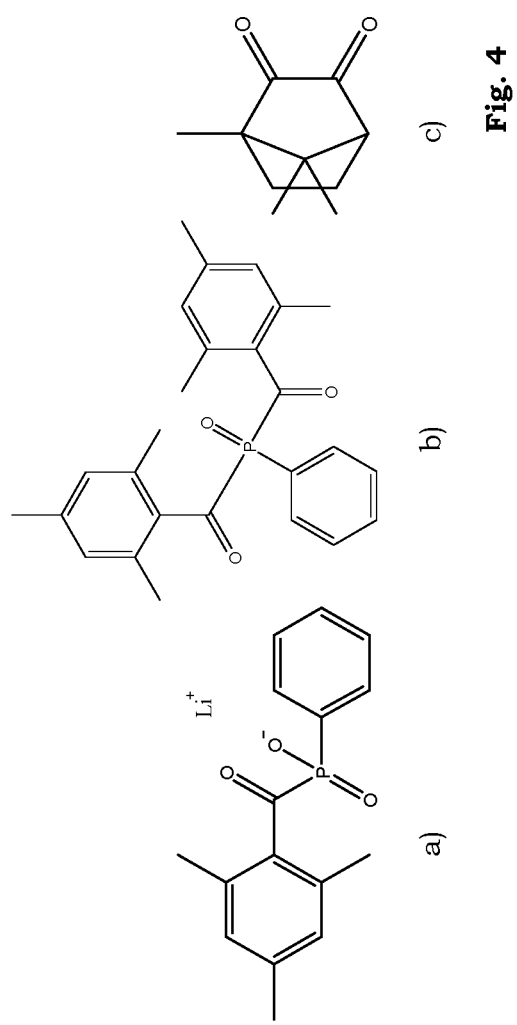
FIG. 4, shows the structure of suitable photoinitiators, Lithium phenyl(2,4,6-trimethylbenzoyl) phosphinate, LAP, b) Bis(mesitoyl)phenylphosphane oxide, Irgacure 819, c) Camphorquinone, CQ.
Figure 5:
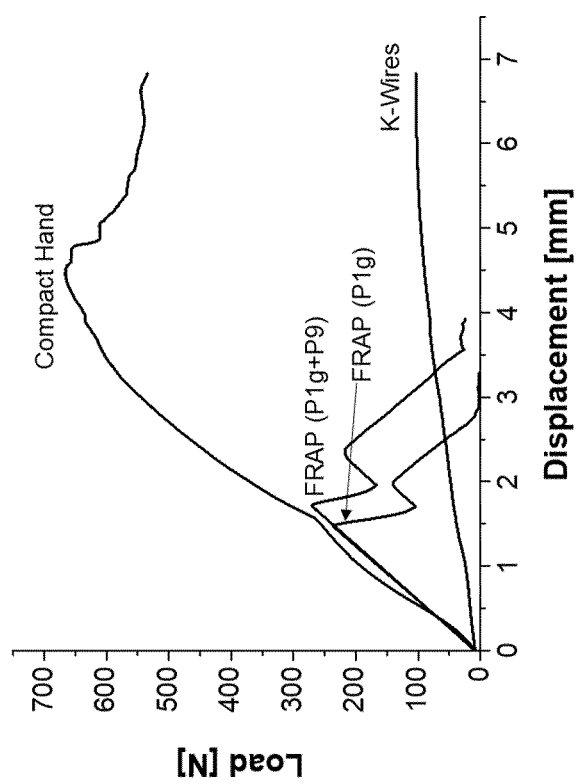
FIG. 5, shows mechanical properties of the present invention.

Any suitable photo initiator may be used. The initiator may be a peroxide, nitrile, phosphine oxide or quinone susceptible to radiation to create reactive species. In one embodiment the photo initiator is selected from lithium phenyl(2,4,6-trimethylbenzoyl)phosphinate (LAP), Irgacure 819, (2,4,6-trimethylbenzoyl)-phosphine oxide (BAPO), diphenyl(2,4,6-trimethylbenzoyl)phosphine oxide (TPO), camphorquinone, carboxylated camphorquinone. FIG. 4 shows some photoinitiators. The amount of photo initiator may be 0.05 to 2 wt % such as 0.1 to 1 wt %.

The composition comprises water which is believed to activate the acid compounds by deprotonation. The water may be present in the form of a mixture of water and an alcohol such as methanol or ethanol, or as a mixture of water and acetone, or a mixture of water, an alcohol and acetone. The weight ratio between the water and the alcohol or acetone may be 1:1 to 1:100 (water:alcohol/acetone). The composition may comprise an alcohol or acetone in an amount of 10-90 wt % such as 40-60 wt % of the total weight of the composition. The amount of water in the composition may be 0.01 to 50 wt % such as 0.5 wt % or more, or 1 wt % or more, or 3 wt % or more, or 5 wt % or more, or 8 wt % or more, but 40 wt % or less, or 30 wt % or less, or 25 wt % or less, or 20 wt % or less, or 15 wt % or less, or 10 wt % or less. The composition is preferably essentially free from benzene or naphthalene compounds since they generally are toxic.

The aqueous composition according to the present invention may also comprise a fourth compound or further compounds comprising at least one allyl containing group or at least one thiol containing group or at least one alkyne.

The Allyl-Phosphonic Acid Containing Compound

The present application also relates to the use of a compound having the general structure of

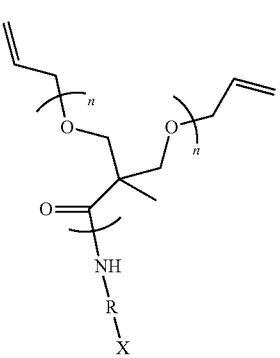

(5)

wherein n is 1 or higher, R is an alkyl group and X is a phosphonic acid containing group. R may be a C1-C10 alkyl group such as a C1-C6 alkyl group. When n is 2 or more the compound is a dendrimer. In one embodiment n is 2 or higher. In another embodiment n is 3 or higher, or 4 or higher. The phosphonic acid group X may be a phosphonic acid or a group having the general structure of

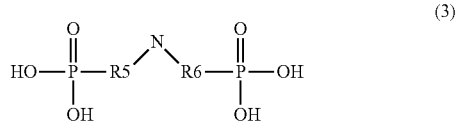

(3)

wherein R5 and R6 are individually an alkyl group such as a methylene or an ethylene group.

The compound may be used as a primer especially for hard tissue such as bone or tooth or metal or synthetic material. The compound may also be used as the second compound of the composition according to the present invention. It may also be used as a coating or a filler for a hard tissue or metal or synthetic material.

Method of Preparing

Here are some general non-limiting examples of how to prepare the present invention.

Phn-G1-(ene)₂ (FIG. 2a)
a. Activating BAPA (FIG. 3c) in EtOAc by reacting with 1,1''-carbonyldiimidazole at 50° C. for at least 30 minutes.
b. Adding Diethyl(aminomethyl)phosphonate and leave it to react at 50° C. for 30 min.
c. Isolating the obtained product EtPhn-G1-(ene)₂.
d. Adding trimethylbromosilane in DCM until completion of reaction, evaporating and subsequently adding methanol.
e. Isolating the obtained product Phn-G1-(ene)₂ (FIG. 2a).

(Phn)₂-EDA-G1-(ene)₂ (FIG. 2b)
a. Activating BAPA (FIG. 3c) in EtOAc by reacting with 1,1''-carbonyldiimidazole at 50° C. for at least 30 minutes.
b. Adding slowly ethylenediamine (EDA) and leave it to react at 50° C. until reaction completion.
c. Isolating the obtained product EDA-G1-(ene)₂.
d. Adding p-formaldehyde in THF and reacting for at least 1 h at 70° C.
e. Adding dropwise dimethylphosphite and leave it to react at 70° C. until reaction completion.
f. Isolating the obtained product MePhn)₂-EDA-G1-(ene)₂.
g. Adding trimethylbromosilane in DCM until completion of reaction, evaporating and subsequently adding methanol.
h. Isolating the obtained product (Phn)₂-EDA-G1-(ene)₂ (FIG. 2b).

Phn-G3-(ene)₈ (FIG. 2d)
a. Activating BAPA (FIG. 3c) in EtOAc by reacting with 1,1''-carbonyldiimidazole at 50° C. for at least 30 minutes.
b. Adding slowly bis-MPA dendron HOOC-G3-(OH)₄ and CsF and leave it to react at 50° C. until reaction completion.
c. Isolating the obtained product HOOC-G3-(ene)₈.
d. Activating compound HOOC-G3-(ene)₈ in EtOAc by reacting with 1,1'-carbonyldiimidazole at 50° C. for at least 30 minutes.
e. Adding Diethyl(aminomethyl)phosphonate and leave it to react at 50° C. for 30 min.
f. Isolating the obtained product EtPhn-G3-(ene)₈.
g. Adding trimethylbromosilane in DCM until completion of reaction, evaporating and subsequently adding methanol.
h. Isolating the obtained product Phn-G3-(ene)₈ (FIG. 2d).

TPYTATO
a. Reacting cyanuric acid and propargyl bromide in DMF in the presence of K₂CO₃ for 16 h at 50° C.
b. Isolate the compound via extraction using DCM and water and finally recrystallization from a solution of 1:1 mixture of methanol and chloroform THYTATO
a. Reacting cyanuric acid and 1-iodo-hexyne in DMSO in the presence of K₂CO₃ for 16 h at 23° C.
b. Isolate the compound via extraction using ethyl acetate and water.

Adhesive Composite

In order to improve the mechanical properties of the primer, especially when used as a patch or a fixation material, an adhesive composite may be applied to the primer before any optional patch or fixation components are applied.

The adhesive composite comprises a photoinitiator, a Component A comprising at least two thiol groups, a Component B comprising vinyl reactive groups chosen from vinyl, acrylate, methacrylate, allyl, unsaturated cyclic vinyls, and alkynes, and optionally a filler, such as a ceramic filler, e.g. calcium phosphate particles or functionalized calcium phosphate particles. Preferably the Component B comprises vinyl reactive groups chosen from vinyl, allyl, unsaturated cyclic vinyls, and alkynes.

Compound A may be selected from the group consisting of pentaerythritol tetrakis(3-mercaptopropionate), trimethylolpropane tris(3-mercaptopropionate), tris 2-(3-mercaptopropionyloxy)ethyl isocyanurate (TEMPIC) 1,3,5-tris(3-mercaptopropyl)-1,3,5-triazinane-2,4,6-trione, mercaptopropyl methylsiloxane-dimethylsiloxane copolymer,poly (mercaptopropyl) methylsiloxane, 2,2' (ethylenedioxy)diethanethiol, ditiotreitol, Tetraethyleneglycol-bis(3-mercaptopropionate), ethyleneglycol-bis(3-mercaptopropionate), trimethylolpropane diallylether, dipentaerytritolhexakis(3-merkaptopropionate), tetradecane-1,14-dithiol, +/−)-trans-1,2-bis (2-mercaptoacetamido) cyclohexane, (E)-S,S'-bis (lo-mercaptodecyl)-4,4'-(diazene-1,2-diyl) bis (4-cyanopentanethioate), bis(2-mercaptoethyl) sulfone, 2,5-dimercaptomethyl-1,4-dithiane, 1,4-butanediol-bis(3-mercaptopropionate), 1,16-hexadecanedithiol, undecane-1,11-dithiol, heptane-1,7-dithiol, 1,12-dimercaptododecane, octadecane-1,18-dithiol, (5-mercaptomethyl-2,4-dimethyl-phenyl)-methanethiol, (3-mercaptomethyl-5-methyl-phenyl)-methanetho, 1,2-benzenedimethanethiol, (4R,5R)-4,5-bis (mercaptomethyl)-2,2-dimethyl-1,3-dioxolane, 3-bis (2-mercaptoethylthio) propane, ethanethiol, aceticacidmercapto-1,2,6-hexanetriyl ester, L-1,4-dithiothretol, glycerylthioglycolate, 3,6-dioxa-1,8-octanedithiol, trimethylolpropane-tris(mercaptoacetate) 2,3-butanediol-1,4-dimercapto-pentaerythritol-tetrakis(3-mercaptopropionate), ethanethiol-2,2',2''-nitrilotris, 2,2'-thiodiethanethiol, 1,9-nonanedithiol, 2,2'-oxydiethanethiol, and 10-decanedithiol.

Compound B may be selected from the group consisting of trimethylolpropane diallyl ether, 1,3,5-triallyl-1,3,5-triazine-2,4,6 (1H,3H,5H)-trione (TATATO), 1,3,5-tri(prop-2-yn-1-yl)-1,3,5-triazinane-2,4,6-trione (TPYTATO), b) 1,3,5-tri(hex-5-yn-1-yl)-1,3,5-triazinane-2,4,6-trione (THYTATO), trimethylolpropane diallyl ether, and poly (ethylene glycol) dimaleinimide.

The molar ratio between thiols and allyls of Compound A and Compound B respectively may be from 1:0.5 to 1:5 such as 1:1 to 1:3 or around 1:2. The molar ratio between thiols and alkynes of Compound A and B respectively may be 1:0.25 to 1:5 such as 1:0.3 to 1:3 or around 1:0.5.

Any suitable photo initiator may be used. The initiator in the adhesive composite may be the same as in the primer or it may be different and preferably it is at least partly soluble in the adhesive composite components. The initiator may be a peroxide, nitrile, phosphine oxide or quinone susceptible to radiation to create reactive species. In one embodiment the photo initiator is selected from lithium phenyl(2,4,6-trimethylbenzoyl)phosphinate (LAP), Irgacure 819, (2,4,6-trimethylbenzoyl)-phosphine oxide (BAPO), diphenyl(2,4, 6-trimethylbenzoyl)phosphine oxide (TPO), camphorquinone, carboxylated camphorquinone.

The adhesive composite may comprise a filler, such as a ceramic filler, e.g. calcium phosphate particles such as hydroxyapatite. The calcium phosphate particles may be functionalized for example with a second compound molecule. The amount of calcium phosphate particles in the composite may be up to 99 wt % such as 90 wt % or less, or 80 wt % or less, or 70 wt % or less, or 60 wt % or less, or 50 wt % or less, or 1 wt % or more, or 10 wt % or more, or 20 wt % or more, or 30 wt % or more, or 40 wt % or more. In one embodiment the amount of calcium phosphate particles is 35-65 wt % or 50-60 wt %.

In one embodiment, none of the second and third layers (i.e. the patch) comprise a filler. In another embodiment, the second and third layers of the adhesive comprise a filler, preferably a ceramic filler, e.g. calcium phosphate particles such as hydroxyapatite. In another embodiment, only the third layer of the adhesive comprises a filler, such as a ceramic filler.

The functionalized calcium phosphate particles may be prepared by mixing the functionalization agent with the particles in a solution. The functionalization agent may be a Second compound molecule and the solution may be an aqueous solution such as a mixture of an alcohol and water. A non-limiting example is disclosed in Example 2.

In one embodiment the amount of Compound A is 10-20 wt %, the amount of Compound B is 20-35 wt % and the amount of calcium phosphate particles or functionalized calcium phosphate particles is 40-70 wt % with proviso that the total amount is not more than 99.9 wt %. In one embodiment the total amount of Compound A, Compound B and calcium phosphate is at least 90 wt %, or at least 95 wt %, or at least 99 wt %, or at least 99.5 wt %.

Applications

The present invention may be used as a primer for example when treating hard tissue such as bone or tooth, or metal or synthetic materials. The primer may be used in combination with a stabilizing device such as patch or with a filler. The patch then comprises a layer of the primer or the compound according to the present invention and on said layer is a layer of a composition comprising the reaction product of at least one component A and at least one component B. Component A comprises a compound comprising at least two thiol groups or a disulfide derivative of a compound comprising at least two thiol groups. Component B comprises vinyl reactive groups chosen from vinyl, acrylates, methacrylates, allyl, unsaturated cyclic vinyls, and alkynes. Preferably the Component B comprises vinyl reactive groups chosen from vinyl, allyl and unsaturated cyclic vinyls, and alkynes. This composition is further described in WO2011048077 which is hereby incorporated by reference. The patch may further comprise fibres such as glass fibres, carbon fibres, polyethylene fibres, cellulose fibres, collagen fibres or polypropylene fibres. In one embodiment, the adhesive composite, alternatively with organic fillers, according to the present invention is applied on top of the primer composition prior to applying the patch, supporting material or filler. The adhesive composite may be applied almost directly after application of the primer composition but in order for the primer to adhere to the tissue and to at least partly cure, the adhesive composite may be applied after 10-60 seconds. The primer can be cured via light irradiation before or after the adhesive is applied, in the latter case the adhesive and primer is cured together. Further layers of the adhesive, alternatively with ceramic fillers can be applied together or without fibers and then cured via light irradiation.

Compound A may be selected from the group consisting of pentaerythritol tetrakis(3-mercaptopropionate), trimethylolpropane tris(3-mercaptopropionate), tris 2-(3-mercaptopropionyloxy)ethyl isocyanurate (TEMPIC), 1,3,5-tris(3-mercaptopropyl)-1,3,5-triazinane-2,4,6-trione, mercaptopropyl methylsiloxane-dimethylsiloxane copolymer,poly (mercaptopropyl) methylsiloxane, 2,2' (ethylenedioxy)diethanethiol, ditiotreitol, Tetraethyleneglycol-bis(3-mercaptopropionate), ethyleneglycol-bis(3-mercaptopropionate), trimethylolpropane diallylether, dipentaerytritolhexakis(3-merkaptopropionate), tetradecane-1,14-dithiol, +/−)-trans-1,2-bis (2-mercaptoacetamido) cyclohexane, (E)-S, S '-bis (10-mercaptodecyl)-4,4'-(diazene-1,2-diyl) bis (4-cyanopentanethioate), bis(2-mercaptoethyl)sulfone, 2,5-dimercaptomethyl-1,4-dithiane, 1,4-butanediol-bis(3-mercaptopropionate), 1,16-hexadecanedithiol, undecane-1,11-dithiol, heptane-1,7-dithiol, 1,12-dimercaptododecane, octadecane-1,18-dithiol, (5-mercaptomethyl-2,4-dimethyl-phenyl)-methanethiol, (3-mercaptomethyl-5-methyl-phenyl)-methanetho, 1,2-benzenedimethanethiol, (4R,5R)-4,5-bis (mercaptomethyl)-2,2-dimethyl-1,3-dioxolane, 3-bis (2-mercaptoethylthio)propane, ethanethiol, aceticacidmercapto-1,2,6-hexanetriyl ester, L-1,4-dithiothretol, glycerylthioglycolate, 3,6-dioxa-1,8-octanedithiol,trimethylolpropane-tris(mercaptoacetate) 2,3-butanediol-1,4-dimercapto-pentaerythritol-tetrakis(3-mercaptopropionate), ethanethiol-2,2',2"-nitrilotris, 2,2'-thiodiethanethiol, 1,9-nonanedithiol, 2,2'-oxydiethanethiol, and 10-decanedithiol.

Compound B may be selected from the group consisting of trimethylolpropane diallyl ether, 1,3,5-triallyl-1,3,5-triazine-2,4,6 (1H,3H,5H)-trione (TATATO), 1,3,5-tri(prop-2-yn-1-yl)-1,3,5-triazinane-2,4,6-trione (TPYTATO), b) 1,3,5-tri(hex-5-yn-1-yl)-1,3,5-triazinane-2,4,6-trione (THYTATO), trimethylolpropane diallyl ether, poly(ethylene glycol)diacrylate, poly(ethylene glycol) dimethacrylate andpoly(ethylene glycol) dimaleinimide.

The patch may further comprise ceramic particles or functionalized ceramic particles. In one embodiment the amount of calcium phosphate particles in the patch is 1-50 wt %.

In one embodiment the patch applied on top of the primer comprises a fiber mesh and TATATO, TEMPIC and a photo initiator (eg. irgacure 819), or TATATO, TEMPIC, photo initiator (eg. irgacure 819) and hydroxyapatite (HA), or TATATO, TEMPIC, photo initiator (eg. irgacure 819) and functionalized HA, or TATATO, TEMPIC and a photo initiator (eg. Camphorquinone (CQ)).

A filler comprising the present composition or compound may also contain particles of a ceramic such as hydroxyapatite or glass. The filler may comprise between 1 to 99 wt % of calcium phosphate particles such as 10 wt % or more, or 30 wt % or more, or 80 wt % or less or 60 wt % or less.

The present invention further relates to calcium phosphate material, surface or particles for example, coated with the composition or the compound according to the present invention.

Curing of the composition may be done using any suitable radiation or light source in order to initiate the reaction. This can be but is not limited to a light emitting diode (LED) polymerization lamp (e.g. Bluephase® 20i) emitting light with wavelengths of 385-515 nm with a dominant wavelength of 470 nm and maximum intensity of 2000-2200 mW/cm$^2$. If more than one layer of the composition or the compound is used each layer may be cured using different irradiation time and intensity.

The present invention presents an improved method of treating bone or tooth fractures or damages. By applying the primer to the hard tissue better mechanical properties are obtained. No other pre-treatments are necessary such as etching of the tissue surface prior to the application of the patch or coating.

Kit

The present invention further relates to a kit in order to provide and apply the primer composition and optionally the adhesive composite. The kit contains at least two suitable containers where one of the containers comprises water; and where one container comprises the first compound having at least two thiol groups, the second compound

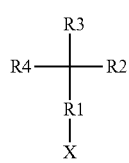
(1)

wherein R1 is an alkyl, a dialkyl ether, dialkyl ester, dialkyl urethane or a dialkyl amide group, R2 is an at least one allyl containing group or an at least one alkyne containing group, R3 is hydrogen, an alkyl group or an at least one allyl containing group or an at least one alkyne containing group and R4 is hydrogen, an alkyl group or an at least one allyl containing group or an at least one alkyne containing group; wherein the first compound or the second compound comprises at least one phosphonic acid containing group X with proviso that when the second compound comprises the at least one phosphonic acid containing group said group is bound to the R1 group.

One of the containers may comprise a third compound or additional compounds comprising at least one allyl containing group or at least one thiol group or at least one alkyne containing group.

The kit further comprises a photo initiator. However in order to avoid reactions in the containers the thiol containing compounds should not be present in the same containers as the allyl containing compounds. The molar ratio between the phosphonic acid groups and the allyl groups in the kit is 0.01 to 0.5.

The kit may further comprise at least two additional containers comprising the components of the adhesive composite i.e. a photoinitiator, a Component A comprising at least two thiol groups, a Component B comprising vinyl reactive groups chosen from vinyl, acrylate, methacrylate, allyl, unsaturated cyclic vinyls, and alkynes and ceramic filler, such as calcium phosphate particles or functionalized calcium phosphate particles. The Component A and Component B may however not be in the same containers in order to avoid reactions in the container.

In one embodiment the containers of the kit are configured to minimize or stop radiation to come in contact with the components or reactants of the containers.

The kit may be in form of one or more at least two compartment syringe. The syringe may comprise a mixing tip. In one embodiment the primer components are arranged in a first at least two compartment syringe and the adhesive composite compounds are arranged in a second at least two compartment syringe.

EXAMPLES

Example 1

Synthesis of Adhesion-Enhancing Components

All reagents and solvents were purchased from commercial sources and used as received unless otherwise stated. 3-(allyloxy)-2-((allyloxy)methyl)-2-methylpropanoic acid (BAPA) was synthesized according to a previously published procedure (P. Antoni, M. J. Robb, L. Campos, M. Montañez, A. Hult, E. Malmström, M. Malkoch, C. J. Hawker, Macromolecules 2010, 43, 6625-6631).

The synthesis of adhesion-enhancing molecules was performed through simplified protocols. The details for some example synthetic approaches are described in the Method of preparing section, in general, the dendritic compounds were prepared by reactions assisted by 1,1″-Carbonyldiimidazole (CDI), resulting in short reaction times, easy purifications and high yields. In brief, BAPA or the BAPA-functionalized dendron was activated with CDI in stoichiometric ratio and subsequently reacted in-situ with the corresponding amino-functional reagent. A simple washing affords the BAPA-derivatives in high yields. Some other reactions were required to obtain the functional materials, including Kabachnik-Fields reaction and phosphonate ester cleavage using Trimethylbromosilane (TMBS).

Example 1.1—Phn-G1-(ene)$_2$ (2a)

In a first step, BAPA (1.5 g, 7.0 mmol) was slowly added over a suspension of CDI (1.2 g, 7.0 mmol) in EtOAc (2 M). The mixture was stirred at 50° C. for 1 h.

Diethyl(aminomethyl)phosphonate (1.0 g, 5.8 mmol) was added to the solution and the reaction proceeded at 50° C. for 30 minutes. The activated acid was quenched by high stirring with water for 1 h and the mixture was diluted with EtOAc and washed with NaHCO$_3$ 10% and NaHSO$_4$ 10%. The organic phase was dried over MgSO$_4$, filtered and evaporated to dryness. Further purification through silica chromatography using EtOAc as elution solvent afforded EtPhn-G1-(ene)$_2$ [$C_{16}H_{30}NO_6P$ (363.4)] as yellow oil (1.3 g, 62% yield).

In a second step, EtPhn-G1-(ene)$_2$ (1.0 g, 2.8 mmol) was dissolved in 2 mL CHCl$_3$ and trimethylbromosilane (910 μL, 6.9 mmol) was slowly added at 0° C. The mixture was stirred at r.t. for 18 h and evaporated to dryness. The residue was redissolved in 2 mL MeOH and stirred at r.t. for 2 h. After solvent evaporation, the residue was redissolved in DCM and evaporated. Phn-G1-(ene)$_2$ (2a) [$C_{12}H_{22}NO_6P$ (307.3)] was isolated as white solid (860 mg, 100% yield).

Example 1.2—(Phn)$_2$-EDA-G1-(ene)$_2$ (2b)

In a first step, BAPA (10.0 g, 0.047 mol) was slowly added over a suspension of CDI (7.8 g, 0.047 mol) in EtOAc (2 M). The mixture was stirred at 50° C. for 1 h and dropwise added to a solution of ethylenediamine (6.2 mL, 0.093 mol) in EtOAc (25 mL) while stirring at 50° C. After 2 h, the mixture was washed with NaHCO$_3$10% (3×). The organic phase was dried over MgSO$_4$, filtered and evaporated to dryness. Further purification through silica chromatography using DCM:NEt$_3$ (99:1) as eluting phase afforded EDA-G1-(ene)$_2$ [C$_{13}$H$_{24}$N$_2$O$_3$ (256.3)] as yellow oil (6.0 g, 50% yield).

In a second step, EDA-G1-(ene)$_2$ (500 mg, 1.95 mmol) and p-formaldehyde (130 mg, 3.90 mmol) were mixed in THF (500 μL). After 1 h at 70° C., dimethylphosphite was added dropwise. The reaction proceeded at 70° C. for 18 h. Then, the solvent was removed under vacuum and the mixture was redissolved in CHCl$_3$ and washed with NaOH 0.1 M (3×). The organic phase was dried over MgSO$_4$, filtered and evaporated to dryness. (MePhn)$_2$-EDA-G1-(ene)$_2$ [C$_{19}$H$_{38}$N$_2$O$_9$P$_2$ (500.5)] was isolated as yellow oil (822 mg, 85% yield).

In a third step, (MePhn)$_2$-EDA-G1-(ene)$_2$ (500 mg, 1.0 mmol) was dissolved in 1 mL CHCl$_3$ and trimethylbromosilane (659 μL, 5.0 mmol) was slowly added at 0° C. The mixture was stirred at r.t. for 18 h and evaporated to dryness. The residue was redissolved in 1 mL MeOH and stirred at r.t. for 2 h. After solvent evaporation, the residue was redissolved in DCM and evaporated. (Phn)$_2$-EDA-G1-(ene)$_2$ (2b) [C$_{15}$H$_{30}$N$_2$O$_9$P$_2$ (444.4)] was isolated as white solid (444 mg, 100% yield).

Example 2

Functionalization of Hydroxyapatite (HA) Particles (Phn)$_2$-EDA-G1-(ene)$_2$ (45 mg, 0.1 mmol) was dissolved in 3 ml MeOH:H$_2$O (1:4). HA particles (4.5 g) were dispersed in the solution and stirred for 5 h. The particles were collected using a filter, rinsed with methanol and evaporated to dryness.

Example 3

Example Compositions

FIG. 7 discloses examples primer compositions.

FIG. 8, description of example adhesive compositions for FRAP

Adhesive Bond Strength

Method 1. Adhesive Shear Bond Strength: FRAP on Bone.

Rectangular bone pieces (4×1.5 cm) were polished to obtain even surfaces and finally sanded using P80 sand paper. The pieces were kept wet with m-SBF (modified Simulated Body Fluid). Fiber reinforced adhesive patches were used to glue bone pieces together in pairs by bridging over the gap between the two bone pieces. Two patches per pair was used in a double-lap shear strength mode to form a more even force distribution. The patches were built up by first wiping the wet bone surface with a tissue cloth and then spreading 1 μl of primer solution on the bonding area of 0.5×0.5 cm of each bone piece. The primer solution was either let to evaporate until a moist state or dried with gentle air-flow. Six consecutive layers of adhesive matrix surrounding five layers of surgical mesh were built up. Curing was induced using a light emitting diode (LED) polymerization lamp (Bluephase® 20i) intended for light-cured dental materials. Bluephase® 20i emits light with wavelengths of 385-515 nm with a dominant wavelength of 470 nm and maximum intensity of 2000-2200 mW/cm$^2$. The first layer was cured with irradiation for 20 s with TURBO mode (2000 mW/cm$^2$), the rest of the layers were irradiated for 10 s with TURBO mode. The patches were submerged in m-SBF directly after final irradiation sequence and stored for 24 h at 37° C. and then let to cool down to 23° C. before testing. Instron 5566 from Instron Korea LLC. with a 10 kN load cell and a cross-head speed of 10 mm/min was used in tensile mode. A pre-load of 1 N and a pre-load speed of 2 mm/min were used. The measurements were conducted at 23° C. and a relative humidity of 50%. The samples were kept wet as long as possible until they were attached to the machine. Data were collected using Bluehill software. Adhesive bond shear strength was calculated from maximum load at break divided by the area of failure. Five specimens of each sample were used.

FIG. 9. Adhesive shear bond strength with different Phosphonic acid/Allyl ratio and pH: FRAP on bone.

Key conclusions: A specific ratio of the adhesion-enhancing group phosphonic acid is needed in a specific ratio range to reach high bond strength. Even though pH of the primer seems to be important it is not enough to just lower the pH with phosphoric acid to reach high bond strength.

FIG. 10. Adhesive shear bond strength with different adhesion enhancing molecules: FRAP on bone.

Key conclusions: The new primer compositions increase the bond strength greatly for the adhesive composite. The new primers together with a thiol-ene or thiol-yne adhesive composite display superior bond strength to wet bone compared to commercial dental adhesives.

Method 2. Adhesive Shear Bond Strength: Adhesive on Bone.

Wet rectangular bone pieces (4×1.5 cm) were polished to obtain even surfaces and finally sanded using P80 sand paper. The pieces were kept wet with m-SBF. Primer solution was applied over an area of 5×5 mm after wiping away excessive water from the bone surface. The primer was dried with gentle airflow and adhesive composite was applied on the primer treated area. Three layers were applied with 10 s curing with TURBO mode in between each layer to build up a drop on the bone piece. The bone pieces were submerged in m-SBF directly after final irradiation sequence and stored for 24 h at 37° C. and then let to cool down to 23° C. before testing. Instron 5566 from Instron Korea LLC. with a 10 kN load cell and a cross-head speed of 5 mm/min was used in compression mode. The bone piece was fixed and the adhesive drop was sheared off by a metal plate. A pre-load of 1 N and a pre-load speed of 2 mm/min were used. The measurements were conducted at 23° C. and a relative humidity of 50%. The samples were kept wet as long as possible until they were attached to the machine. Data were collected using Bluehill software. Adhesive bond shear strength was calculated from maximum load at break divided by the area of failure. Five specimens of each sample were used.

FIG. 11. Adhesive shear bond strength: Adhesive on bone.

Key conclusions: The new primer compositions together with a thiol-ene adhesive composite display superior bond strength to wet bone compared to a commercial dental restoration system.

Method 3. Adhesive Shear Bond Strength: Adhesive on Porcine Bone.

Shear bond strength tests was performed using an Instron 5566 instrument, Instron Korea LLC. A 500 N load cell and a cross-head speed of 5 mm/min in compression mode with a pre-load of 1 N and a pre-load speed of 2 mm/min. The measurements were conducted at 23° C. and a relative humidity of 50%. Porcine metacarpals where the soft tissue had been removed and the bone cut into two pieces were used as substrates. The bone surface was roughened with an abrasive pin and then wiped with a wet tissue cloth. First a primer was applied in an amount of 4 μl/cm2 and dried with gentle air-flow. Then an adhesive resin was applied as a drop and cured with 20 s of irradiation with Bluephase 20i with TURBO mode (λ=385-515 nm, 2000 mW/cm2). The bones were kept in wet tissue before and after sample preparation to maintain moist conditions. The dental adhesive reference was applied on both substrates in a similar fashion but adjusted to the intended application procedure from the manufacturers. Five specimens of each sample were tested.

FIG. 14. Adhesive shear bond strength: Adhesive on porcine metacarpal.

Key conclusions: The thiol-yne adhesive show higher adhesion than the thiol-ene adhesive and with a primer containing a large amount of alkyne monomer and reduced amount of allyl monomer increased the bond strength further for the thiol-yne adhesive Method 4. Adhesive Shear Bond Strength: Adhesive on Contaminated Bone.

Wet rectangular bone pieces (4×1.5 cm) were polished to obtain even surfaces and finally sanded using P80 sand paper. The pieces were kept wet with m-SBF. Bovine blood serum was applied onto the bone surfaces and dried with gentle airflow to form a contaminating protein layer. Primer solution was applied over an area of 5×5 mm on the contaminated bone surface and brushed into the surface using a tuft brush. The adhesive composite was applied on the primer treated area. Three layers were applied with 10 s curing with TURBO mode in between each layer to build up a drop on the bone piece. The bone pieces were submerged in m-SBF directly after final irradiation sequence and stored for 24 h at 37° C. and then let to cool down to 23° C. before testing. Instron 5566 from Instron Korea LLC. with a 500 N load cell and a cross-head speed of 5 mm/min was used in compression mode. The bone piece was fixed and the adhesive drop was sheared off by a metal plate. A pre-load of 1 N and a pre-load speed of 2 mm/min were used. The measurements were conducted at 23° C. and a relative humidity of 50%. The samples were kept wet as long as possible until they were attached to the machine. Data were collected using Bluehill software. Adhesive bond shear strength was calculated from maximum load at break divided by the area of failure. Three specimens of each sample were used.

FIG. 15. Adhesive shear bond strength: Adhesive on contaminated bone.

Key conclusions: The primer composition P10 containing an alkyne component formed a much stronger bond to the contaminated bone surface than primer composition P1f.

Method 5. FRAP Fixation of Phalangeal Fracture Model.

Fracture fixation was tested using the second and the fifth metacarpals of domestic pigs. Surrounding soft tissue and periosteum were removed from the bones. A transverse fracture was created on each bone using a saw. The bones were washed with water and then wrapped in cloth soaked in amoxicillin solution to keep the bones wet and prevent bacterial growth. FRAP technology with primer composition P1b and adhesive composite A2 was used to fixate the fractures. As comparative control fixations with one method with two crossed Kirschner wires 1.0 and one method with Compact hand Locking Strut Plate 1.5 were used. Three-point bending was performed with a distance of 3 mm between the lower contacts in an Instron 5566 (Instron Korea LLC) with a 10 kN load cell and a cross-head speed of 10 mm/min. The measurements were conducted at 23° C. and a relative humidity of 50%. The samples were kept wet as long as possible until they were attached on the bending apparatus. Data were collected using Bluehill software. Five specimens of each fixation method were tested.

FIG. 12. Bending rigidity and maximum bending moment of a FRAP containing primer P1b compared to conventional finger fixations of K-wire 1.0 and Compact hand 1.5.

Key conclusions: The new primer systems provides enough bond strength to enable that FRAP fixation gives superior support to K-wires and can even compete with the screw fixated metal plate in the load range of interest.

Method 6. Adhesive Shear Bond Strength: Adhesive on Dentin.

In the first test set-up, roe dear teeth were polished to expose the dentin and obtain even surfaces and finally sanded using P80 sand paper. The teeth were kept wet with m-SBF. Primer solution was applied over an area of 5×5 mm after wiping away excessive water from the tooth surface. The primer was dried with gentle airflow and adhesive composite was applied on the primer treated area. Three layers were applied with 10 s curing with TURBO mode in between each layer to build up a drop on the tooth. The teeth were submerged in m-SBF directly after final irradiation sequence and stored for 24 h at 37° C. and then let to cool down to 23° C. before testing. Instron 5566 from Instron Korea LLC. with a 10 kN load cell and a cross-head speed of 5 mm/min was used in compression mode. The tooth was fixed and the adhesive drop was sheared off by a metal plate. A pre-load of 1 N and a pre-load speed of 2 mm/min were used. The measurements were conducted at 23° C. and a relative humidity of 50%. The samples were kept wet as long as possible until they were attached to the machine. Data were collected using Bluehill software. Adhesive bond shear strength was calculated from maximum load at break divided by the area of failure. Five specimens of each sample were used. The second test substrate was human dental enamel where the surface had been smoothened with a rotary cutter and then wiped with a wet tissue cloth. First a primer was applied in an amount of 4 μl/cm2 and dried with gentle air-flow. Then an adhesive resin was applied as a thin layer and cured with 20 s of irradiation with Bluephase 20i. Then a composite was applied as a drop and cured with 20 s of irradiation with Bluephase 20i. The teeth were kept in water before and after sample preparation to maintain wet conditions. The dental adhesive reference was applied on both substrates in a similar fashion but adjusted to the intended application procedure from the manufacturers. Five specimens of each sample were tested.

FIG. 13. Adhesive shear bond strength: Adhesive on dentin and enamel.

Key conclusions: The new primer together with a thiol-ene adhesive composite display at least as high bond strength to wet dentine compared to a commercial dental restoration system. The primer composition constituting of alkyne to a major part together with an thiol-yne adhesive as second layer and an thiol-yne adhesive composite as a third layer displayed extremely good adhesion to human enamel compared to a commercial dental restoration system.

Method 7. Adhesive Shear Bond Strength: Adhesive on Steel.

Primer solution was applied on steel over an area of 5×5 mm. The primer was dried with gentle airflow and adhesive composite was applied on the primer treated area. Three layers were applied with 10 s curing with TURBO mode in between each layer to build up a drop on the steel plate. The steel plate was submerged in m-SBF directly after final irradiation sequence and stored for 24 h at 37° C. and then let to cool down to 23° C. before testing. Instron 5566 from Instron Korea LLC. with a 10 kN load cell and a cross-head speed of 5 mm/min was used in compression mode. The metal plate was fixed and the adhesive drop was sheared off by a second metal plate. A pre-load of 1 N and a pre-load speed of 2 mm/min were used. The measurements were conducted at 23° C. and a relative humidity of 50%. The samples were kept wet as long as possible until they were attached to the machine. Data were collected using Bluehill software. Adhesive bond shear strength was calculated from maximum load at break divided by the area of failure. Five specimens of each sample were used.

FIG. 14. Adhesive shear bond strength with different Phosphonic acid/Allyl ratio and pH: Adhesive on steel.

Key conclusions: A specific ratio of phosphonic acid and allyl is needed to reach high bond strength. Less phosphonic acid is needed on steel compared to bone to reach high bond strength.

The invention claimed is:

1. An aqueous composition comprising
   a first compound having at least two thiol groups;
   a second compound having the general structure of

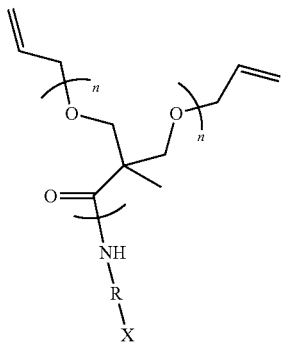

(5)

wherein n is 1 or higher, R is an alkyl group and X is a phosphonic acid containing group; and
   a third compound or additional compounds comprising at least one alkyne containing group;
   a photo initiator.

2. The aqueous composition according to claim 1 wherein the pH of the composition is in the range of 1.5 to 4.

3. The aqueous composition according to claim 1, wherein the molar ratio between the phosphonic acid groups and the allyl groups in the composition is 0.01 to 4.

4. The aqueous composition according to claim 3 wherein the molar ratio between the phosphonic acid groups and the allyl groups is 0.01-3.

5. The aqueous composition according to claim 1 wherein the molar ratio between the phosphonic acid groups and the thiols groups is 0.01 to 0.5.

6. The aqueous composition according to claim 1 wherein the molar ratio between the phosphonic acid groups and the alkyne groups is 0.02 to 1.

7. The aqueous composition according to claim 1 wherein the molar ratio between allyl groups and alkyne groups is 0.02 to 2.

8. The aqueous composition according to claim 1 wherein each of the at least one alkyne containing group is an alkyl alkyne group containing one or more alkyne groups, or each of the at least one alkyne containing group is a dialkyl ether alkyne group containing one or more alkyne groups.

9. The aqueous composition according to claim 1 wherein the third compound or additional compounds is a dendrimer having two or more alkyne groups.

10. The aqueous composition according to claim 1 wherein the phosphonic acid containing group of the second compound has the structure of:

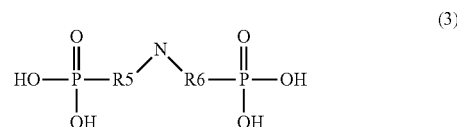

(3)

wherein R5 and R6 are individually an alkyl group.

11. The aqueous composition according to claim 1 wherein the second compound comprises at least one phosphonic acid containing group and wherein the composition comprises a third compound having the general structure of

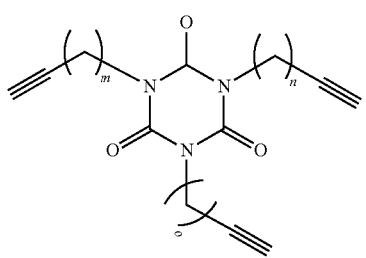

wherein m, n and o is 1 or higher.

12. The aqueous composition according to claim 1 wherein the first compound is selected from tris 2-(3-mercaptopropionyloxy)ethyl isocyanurate (TEMPIC), ethoxylated-trimethylolpropane tri-3-mercaptopropionate (ETTMP), trimethylolpropane tri-3-mercaptopropionate, thiolated poly(ethylene glycol), 1,3,5-tris(3-mercaptopropyl)-1,3,5-triazinane-2,4,6-trione (TTTSH) and ethoxylated-trimethylolpropane tri-thiol (ETTT) and thiolated multi armed poly(ethylene glycol).

13. The aqueous composition according to claim 1 wherein the composition comprises a third compound selected from 1,3,5-tri(prop-2-yn-1-yl)-1,3,5-triazinane-2,4,6-trione (TPYTATO), 1,3,5-tri(hex-5-yn-1-yl)-1,3,5-triazinane-2,4,6-trione (THYTATO), Bis(propynyloxymethyl) propanoic acid (BPPA).

14. The aqueous composition according to claim 1 wherein the total amount of the second compound and third compound is 1-10 wt %.

15. The aqueous composition according to claim 1 further comprising a fourth compound or additional compounds comprising at least one allyl containing group or at least one thiol containing group or at least one alkyne.

16. A patch comprising
   a first layer or primer layer comprising the composition according to claim 1;
   a second layer of adhesive comprising photoinitiator, a Component A comprising at least two thiol groups, a Component B comprising vinyl reactive groups chosen from vinyl, acrylate, methacrylate, allyl and unsaturated cyclic vinyls, or alkynes; and
   Optionally a third layer comprising Component A comprising at least two thiol groups, a Component B comprising vinyl reactive groups chosen from vinyl, acrylate, methacrylate, allyl and unsaturated cyclic vinyls, or alkynes.

17. The patch according to claim 16 comprising a filler.

18. The patch according to claim 17 wherein the filler is a ceramic filler.

19. The patch according to claim 16 wherein the composition provided on the primer layer further comprises fibres.

20. A calcium phosphate material having a coating comprising the composition according to claim 1.

21. A kit comprising at least two containers wherein any one container in the kit can contain any of water;
a first compound having at least two thiol groups;
a second compound having the general structure of

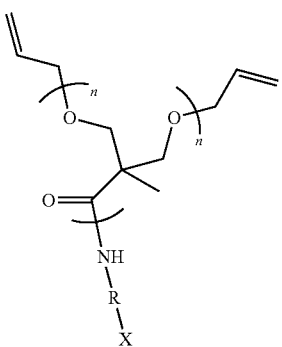

(5)

Wherein n is 1 or higher, R is an alkyl group and X is a phosphonic acid containing group;

a third compound or additional compounds comprising at least one alkyne containing group;

and a photo initiator.

22. The kit according to claim 21 wherein the kit comprises at least two additional containers wherein
any one container in the kit can contain any of a photo initiator, a Component A comprising at least two thiol groups, a Component B comprising vinyl reactive groups chosen from vinyl, acrylate, methacrylate, allyl and unsaturated cyclic vinyls, or alkynes and optionally calcium phosphate particles or functionalized calcium phosphate particles;

with proviso that the Component A is not present in the same container as the Component B.

23. The kit according to claim 22 wherein the kit comprises calcium phosphate particles or functionalized calcium phosphate particles.

* * * * *